United States Patent
Makino et al.

(10) Patent No.: US 10,005,722 B2
(45) Date of Patent: *Jun. 26, 2018

(54) KETENE IMINE COMPOUND, POLYESTER FILM, BACK SHEET FOR SOLAR CELL MODULE, AND SOLAR CELL MODULE

(71) Applicant: FUJIFILM Corporation, Tokyo (JP)

(72) Inventors: Masaomi Makino, Shizuoka (JP); Shigeki Uehira, Shizuoka (JP); Makoto Fukuda, Shizuoka (JP); Masatoshi Mizumura, Shizuoka (JP); Michihiro Ogawa, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 319 days.

This patent is subject to a terminal disclaimer.

(21) Appl. No.: 14/850,361

(22) Filed: Sep. 10, 2015

(65) Prior Publication Data

US 2016/0002150 A1 Jan. 7, 2016

Related U.S. Application Data

(63) Continuation of application No. PCT/JP2014/056281, filed on Mar. 11, 2014.

(30) Foreign Application Priority Data

Mar. 12, 2013 (JP) .................... 2013-049370
Jan. 21, 2014 (JP) .................... 2014-008327

(51) Int. Cl.

| C07C 251/16 | (2006.01) |
|---|---|
| C08K 5/29 | (2006.01) |
| H01L 31/049 | (2014.01) |
| C08J 5/18 | (2006.01) |
| C08K 3/22 | (2006.01) |
| H01L 31/0232 | (2014.01) |

(52) U.S. Cl.
CPC .............. *C07C 251/16* (2013.01); *C08J 5/18* (2013.01); *C08K 3/22* (2013.01); *C08K 5/29* (2013.01); *H01L 31/02327* (2013.01); *H01L 31/049* (2014.12); *C08J 2367/03* (2013.01); *C08K 2003/2241* (2013.01); *Y02E 10/50* (2013.01)

(58) Field of Classification Search
CPC ................ C07C 251/16; H01L 31/049; H01L 31/02327; C08J 5/18; C08K 3/22; C08K 5/29

See application file for complete search history.

(56) References Cited

U.S. PATENT DOCUMENTS

| 3,692,745 A | 9/1972 | Molenaar |
|---|---|---|
| 5,763,538 A | 6/1998 | Hunter et al. |
| 2015/0232419 A1 | 8/2015 | Uehira et al. |

FOREIGN PATENT DOCUMENTS

| CN | 104781340 A | 7/2015 |
|---|---|---|
| JP | H10-130482 A | 5/1998 |

OTHER PUBLICATIONS

Sikkema et al. Reactive additives for polyethylene terephthalate I. Preparation of Ketenimines. Journal of the Royal Netherlands Chemical Society, 1976, p. 154-156.*
International Search Report issued in PCT/JP2014/056281 dated May 27, 2014.
Written Opinion issued in PCT/JP2014/056281 dated May 27, 2014.
First Office Action issued by the State Intellectual Property Office of People's Republic of China dated Jun. 3, 2016, in connection with Chinese Patent Application No. 201480014265.5.
Leo F. Clarke et al., Relatively Stable N-Benzhydryl- and N-Benzyldiarylketene Imines and Their Conversion to Cyanodiarylmethanes via an Isolable Radical, J. Org. Chem., 1992, 362-366, 57, Chemistry Department, University College Dublin, Dublin 4, Ireland.
International Preliminary Report on Patentability issued by WIPO dated Sep. 15, 2015 in connection with Intl. Patent Application No. PCT/JP2014/056281.

* cited by examiner

*Primary Examiner* — John E Uselding
(74) *Attorney, Agent, or Firm* — Edward Neils LLC; Jean C. Edwards, Esq.

(57) ABSTRACT

A polyester resin composition including a ketene imine compound represented by the Formula (1) and polyester shows excellent hydrolysis resistance and prevents yellowing. At least one of $R_{11}$, $R_{12}$, $R_{21}$ and $R_{22}$ represents an alkyl, aryl, alkoxy or aryloxy group which may have a substituent; $R_{15}$ and $R_{25}$ represent an alkyl, aryl, alkoxy or aryloxy group which may have a substituent; $R_3$ represents an alkyl or aryl group which may have a substituent; and a and b represent an integer of 0 to 3.

General Formula (1)

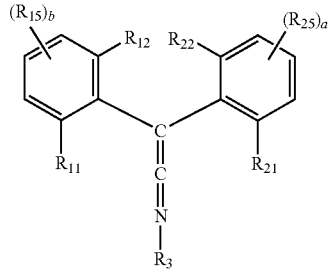

22 Claims, No Drawings

KETENE IMINE COMPOUND, POLYESTER FILM, BACK SHEET FOR SOLAR CELL MODULE, AND SOLAR CELL MODULE

CROSS-REFERENCE TO RELATED APPLICATIONS

This application is a Continuation of PCT International Application No. PCT/JP2014/056281, filed on Mar. 11, 2014, which was published under PCT Article 21(2) in Japanese, and claims priority under 35 U.S.C. Section 119(a) to Japanese Patent Application No. 2013-049370 filed on Mar. 12, 2013, and Japanese Patent Application No. 2014-008327 filed on Jan. 21, 2014. The above applications are hereby expressly incorporated by reference, in their entirety, into the present application.

BACKGROUND OF THE INVENTION

Field of the Invention

The present invention relates to a ketene imine compound, a polyester film, a back sheet for a solar cell module, and a solar cell module.

Background Art

A solar cell module generally has a laminate structure in which a glass or front sheet/a transparent filling material (sealing material)/a solar cell element/a sealing material/a back sheet are laminated in this order from the light-receiving surface side to which sunlight is incident. The solar cell element is generally embedded with a resin (sealing material) such as EVA (ethylene-vinyl acetate copolymer) or the like, and a protective sheet for a solar cell is further adhered thereto. In the protective sheet for a solar cell, in particular, a back sheet for a solar cell module which is disposed on the outermost layer protects the solar cell element. However, in a case where the solar cell module is installed on a stage, the back sheet is considered to be exposed to wind or rain, or to be placed under an environment of high temperature and high humidity for a long period of time, and therefore, excellent weather resistance is required.

As the back sheet for a solar cell module, in the related art, a polyester film, in particular, a polyethylene terephthalate (hereinafter, referred to as PET) film has been used. The polyester film has excellent heat resistance, mechanical characteristics, chemical resistance, and the like, and therefore, the polyester film is preferably used in the back sheet for a solar cell module. However, since the film has poor hydrolysis resistance, the molecular weight is reduced by hydrolysis, and mechanical properties are reduced by progressively stiffening, and thus, it is not possible to maintain a practical strength for a long period of time as a back sheet for a solar cell.

Patent Document 1 and Patent Document 2 propose to add a ketene imine compound as a terminal blocking agent to the polyester film in order to increase the hydrolysis resistance of the polyester film. Here, the ketene imine compound suppresses hydrolysis of polyester by reacting with the terminal carboxyl group of the polyester.

CITATION LIST

Patent Documents

Patent Document 1: U.S. Pat. No. 3,692,745
Patent Document 2: JP-A-10-130482

SUMMARY OF INVENTION

As proposed in Patent Document 1 and Patent Document 2, by incorporating a ketene imine compound into a polyester film, it is possible to improve the hydrolysis resistance of the polyester film. However, as a result of studies of the present inventors, it was found that, when a ketene imine compound is incorporated into a polyester film, the polyester film is yellowed. In the case of using such a polyester film as a back sheet of a solar cell module, the light reflectance of the back sheet is reduced, and the power generation efficiency of a solar cell module decreases, and therefore, these become a problem.

In addition, in the case of using a colored polyester film as a back sheet of a solar cell module, there is a problem that the design characteristics of the entirety of the solar cell module are deteriorated.

Therefore, in order to solve such problems in the related art, the present inventors have conducted studies for the purpose of providing a polyester film having improved hydrolysis resistance in which yellowing is reduced.

As a result of thorough studies in order to solve the above problems, the present inventors found that, by using a ketene imine compound having a specific structure, the hydrolysis resistance of the polyester film is increased, and the polyester film is prevented from being yellowed.

Specifically, the present invention has the following configurations.

[1] A polyester resin composition including a ketene imine compound represented by the following Formula (1) and polyester.

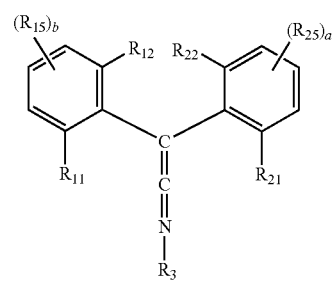

General Formula (1)

In Formula (1), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent, and $R_{15}$ and $R_{25}$ each independently represent an alkyl group which may have a substituent, an aryl group which may have a substituent, an alkoxy group which may have a substituent, or an aryloxy group which may have a substituent. Moreover, $R_{11}$, $R_{12}$, or $R_{15}$ may form a condensed ring by the substituents adjacent to each other, and $R_{21}$, $R_{22}$, or $R_{25}$ may form a condensed ring by the substituents adjacent to each other. $R_3$ represents an alkyl group which may have a substituent or an aryl group which may have a substituent. In addition, a and b each independently represent an integer of 0 to 3.

[2] The polyester resin composition according to [1], in which the ketene imine compound is represented by the following Formula (2).

General Formula (2)

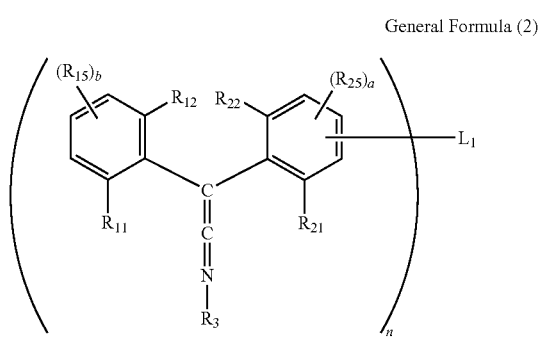

In Formula (2), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent, and $R_{15}$ and $R_{25}$ each independently represent an alkyl group which may have a substituent, an aryl group which may have a substituent, an alkoxy group which may have a substituent, or an aryloxy group which may have a substituent. Moreover, $R_{11}$, $R_{12}$, or $R_{15}$ may form a condensed ring by the substituents adjacent to each other, and $R_{21}$, $R_{22}$, or $R_{25}$ may form a condensed ring by the substituents adjacent to each other. $R_3$ represents an alkyl group which may have a substituent or an aryl group which may have a substituent. In addition, a represents an integer of 0 to 2, and b represents an integer of 0 to 3. n represents an integer of 1 to 4, and $L_1$ represents an n valent linking group.

[3] The polyester resin composition according to [1], in which the ketene imine compound is represented by the following Formula (3-1).

General Formula (3-1)

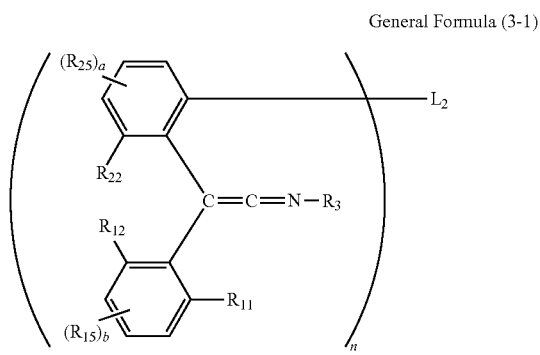

In Formula (3-1), at least one of $R_{11}$, $R_{12}$, and $R_{22}$ each independently represents an alkyl group which may have a substituent, an aryl group which may have a substituent, an alkoxy group which may have a substituent, or an aryloxy group which may have a substituent, and $R_{15}$ and $R_{25}$ each independently represent an alkyl group which may have a substituent, an aryl group which may have a substituent, an alkoxy group which may have a substituent, or an aryloxy group which may have a substituent. Moreover, $R_{11}$, $R_{12}$, or $R_{15}$ may form a condensed ring by the substituents adjacent to each other, and $R_{22}$ or $R_{25}$ may form a condensed ring by the substituents adjacent to each other. $R_3$ represents an alkyl group which may have a substituent or an aryl group which may have a substituent. In addition, a and b each independently represent an integer of 0 to 3. n represents an integer of 1 to 4, and $L_2$ represents an n valent linking group.

[4] The polyester resin composition according to [1], in which the ketene imine compound is represented by the following Formula (3-2).

General Formula (3-2)

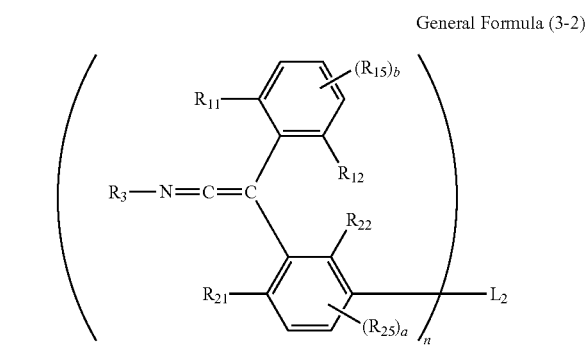

In Formula (3-2), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent, and $R_{15}$ and $R_{25}$ each independently represent an alkyl group which may have a substituent, an aryl group which may have a substituent, an alkoxy group which may have a substituent, or an aryloxy group which may have a substituent. Moreover, $R_{11}$, $R_{12}$, or $R_{15}$ may form a condensed ring by the substituents adjacent to each other, and $R_{21}$ or $R_{25}$ may form a condensed ring by the substituents adjacent to each other. $R_3$ represents an alkyl group which may have a substituent or an aryl group which may have a substituent. In addition, a represents an integer of 0 to 2, and b represents an integer of 0 to 3. n represents an integer of 1 to 4, and $L_2$ represents an n valent linking group.

[5] The polyester resin composition according to [1], in which the ketene imine compound is represented by the following Formula (4).

General Formula (4)

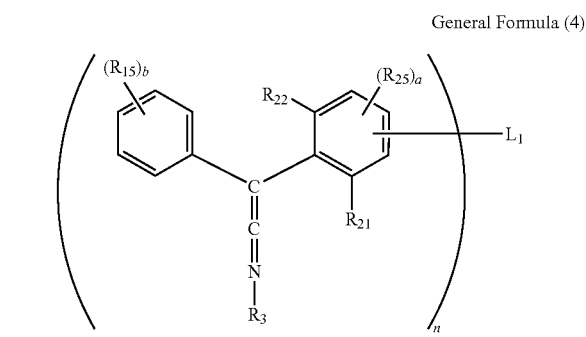

In Formula (4), at least one of $R_{21}$ and $R_{22}$ each independently represents an alkyl group which may have a substituent, an aryl group which may have a substituent, an alkoxy group which may have a substituent, or an aryloxy group which may have a substituent. $R_{15}$ and $R_{25}$ each independently represent an alkyl group which may have a substituent, an aryl group which may have a substituent, an alkoxy group which may have a substituent, or an aryloxy group which may have a substituent. Moreover, $R_{15}$ may form a condensed ring by the substituents adjacent to each other, and $R_{21}$, $R_{22}$, or $R_{25}$ may form a condensed ring by the substituents adjacent to each other. $R_3$ represents an alkyl group which may have a substituent or an aryl group which may have a substituent. In addition, a represents an integer of 0 to 2, and b represents an integer of 0 to 5. n represents an integer of 1 to 4, and $L_1$ represents an n valent linking group.

[6] The polyester resin composition according to [5], in which at least one of $R_{21}$ and $R_{22}$ in the above-described Formula (4) represents an alkoxy group which may have a substituent or an aryloxy group which may have a substituent.

[7] The polyester resin composition according to [5] or [6], in which $R_{22}$ in the above-described Formula (4) represents an alkoxy group which may have a substituent or an aryloxy group which may have a substituent.

[8] The polyester resin composition according to [1], in which the ketene imine compound is represented by the following Formula (5).

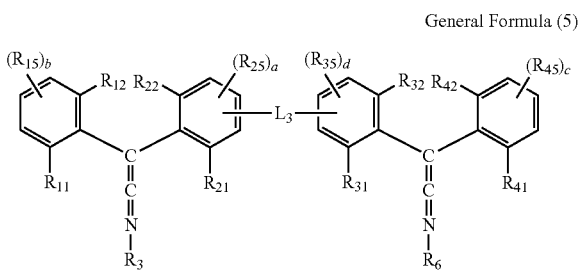

General Formula (5)

In Formula (5), at least one of $R_{11}$, $R_{12}$, $R_{21}$, $R_{22}$, $R_{31}$, $R_{22}$, $R_{41}$, and $R_{42}$ each independently represents an alkyl group which may have a substituent, an aryl group which may have a substituent, an alkoxy group which may have a substituent, or an aryloxy group which may have a substituent. $R_{15}$, $R_{25}$, $R_{35}$, and $R_{45}$ each independently represent an alkyl group which may have a substituent, an aryl group which may have a substituent, an alkoxy group which may have a substituent, or an aryloxy group which may have a substituent. Moreover, $R_{11}$, $R_{12}$, or $R_{15}$ may form a condensed ring by the substituents adjacent to each other, $R_{21}$, $R_{22}$ or $R_{25}$ may form a condensed ring by the substituents adjacent to each other, $R_{31}$, $R_{32}$, or $R_{35}$ may form a condensed ring by the substituents adjacent to each other, and $R_{41}$, $R_{42}$, or $R_{45}$ may form a condensed ring by the substituents adjacent to each other. $R_3$ and $R_6$ each represent an alkyl group which may have a substituent or an aryl group which may have a substituent. In addition, a and b each independently represent an integer of 0 to 2, and b and c each independently represent an integer of 0 to 3. $L_3$ represents a single bond or a divalent linking group.

[9] The polyester resin composition according to [8], in which at least one of $R_{11}$, $R_{12}$, $R_{21}$, $R_{22}$, $R_{31}$, $R_{32}$, $R_{41}$, and $R_{42}$ in the above-described Formula (5) represents an alkoxy group which may have a substituent or an aryloxy group which may have a substituent.

[10] The polyester resin composition according to [8] or [9], in which at least one of $R_{21}$, $R_{22}$, $R_{31}$, and $R_{32}$ in the above-described Formula (5) represents an alkoxy group which may have a substituent or an aryloxy group which may have a substituent.

[11] The polyester resin composition according to any one of [1] to [10], in which the molecular weight of the ketene imine compound is 500 or greater.

[12] The polyester resin composition according to any of [1] to [11], in which the ketene imine value (the total molecular weight/the number of functional groups of ketene imine) of the ketene imine compound is 420 or less.

[13] The polyester resin composition according to any of [1] to [12], in which the ketene imine compound is contained in 0.1% by mass to 2.0% by mass with respect to the polyester.

[14] The polyester resin composition according to any of [1] to [13], which further includes a pigment.

[15] The polyester resin composition according to [14], in which the pigment is titanium oxide.

[16] A polyester film formed of the polyester resin composition according to any of [1] to [15].

[17] A back sheet for a solar cell module having the polyester film according to [16].

[18] A solar cell module having the back sheet for a solar cell module according to [17].

[19] A ketene imine compound represented by Formula (6).

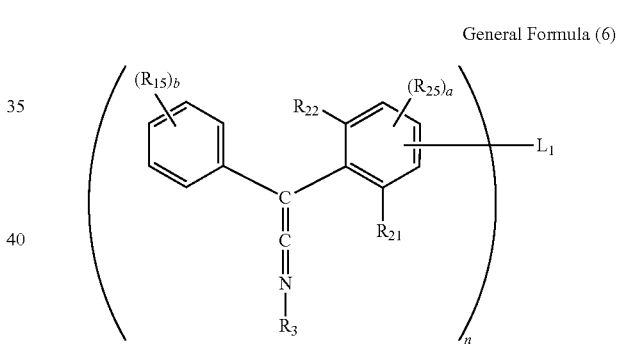

General Formula (6)

In Formula (6), at least one of $R_{21}$ and $R_{22}$ represents an alkoxy group which may have a substituent or an aryloxy group which may have a substituent. $R_{15}$ and $R_{25}$ each independently represent an alkyl group which may have a substituent, an aryl group which may have a substituent, an alkoxy group which may have a substituent, or an aryloxy group which may have a substituent. Moreover, $R_{15}$ may form a condensed ring by the substituents adjacent to each other, and $R_{21}$, $R_{22}$, or $R_{25}$ may form a condensed ring by the substituents adjacent to each other. $R_3$ represents an alkyl group which may have a substituent or an aryl group which may have a substituent. In addition, a represents an integer of 0 to 2, and b represents an integer of 0 to 5. n represents an integer of 1 to 4, and $L_1$ represents an n valent linking group.

[20] The ketene imine compound according to [19], in which $R_{22}$ in the above-described Formula (6) represents an alkoxy group which may have a substituent or an aryloxy group which may have a substituent.

[21] The ketene imine compound according to [19], which is represented by the following Formula (7).

General Formula (7)

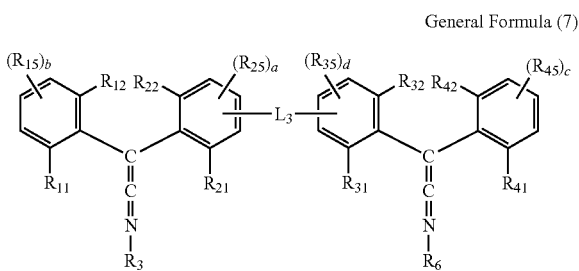

In Formula (7), at least one of $R_{11}$, $R_{12}$, $R_{21}$, $R_{22}$, $R_{31}$, $R_{32}$, $R_{41}$, and $R_{42}$ represents an alkoxy group which may have a substituent or an aryloxy group which may have a substituent. $R_{15}$, $R_{25}$, $R_{35}$, and $R_{45}$ each independently represent an alkyl group which may have a substituent, an aryl group which may have a substituent, an alkoxy group which may have a substituent, or an aryloxy group which may have a substituent. Moreover, $R_{11}$, $R_{12}$, or $R_{15}$ may form a condensed ring by the substituents adjacent to each other, $R_{21}$, $R_{22}$ or $R_{25}$ may form a condensed ring by the substituents adjacent to each other, $R_{31}$, $R_{32}$, or $R_{35}$ may form a condensed ring by the substituents adjacent to each other, and $R_{41}$, $R_{42}$, or $R_{45}$ may form a condensed ring by the substituents adjacent to each other. $R_3$ and $R_6$ each represent an alkyl group which may have a substituent or an aryl group which may have a substituent. In addition, a and b each independently represent an integer of 0 to 2, and b and c each independently represent an integer of 0 to 3. $L_3$ represents a single bond or a divalent linking group.

[22] The ketene imine compound according to [21], in which at least one of $R_{21}$, $R_{22}$, $R_{31}$, and $R_{32}$ in the above-described Formula (7) represents an alkoxy group which may have a substituent or an aryloxy group which may have a substituent.

According to the present invention, by using a ketene imine compound having a specific structure, the hydrolysis resistance of a polyester film is increased, and the polyester film is prevented from being yellowed. Thus, it is possible to increase the light reflectance of a back sheet for a solar cell module, and it is possible to increase the power generation efficiency of a solar cell module. In addition, by suppressing yellowing of a polyester film, it is possible to obtain a back sheet for a solar cell module having excellent design characteristics.

Furthermore, according to the present invention, when the ketene imine compound has a certain level or greater of molecular weight, it is possible to suppress volatilization of the ketene imine compound in the production step. Thus, it is possible to obtain an additional effect in which the production suitability can be increased.

DESCRIPTION OF EMBODIMENTS

Hereinafter, the present invention will be described in detail. The description of the constitutive elements as described below is based on representative embodiments or specific examples, but the present invention is not limited to such embodiments. Further, in the specification, the range with the numerical value indicated by "from (a lower limit) to (an upper limit)" means a range that falls between the former number indicating the lower limit of the range and the latter number indicating the upper limit thereof.

(Ketene Imine Compound)

The ketene imine compound used in the present invention is represented by the following Formula (1).

General Formula (1)

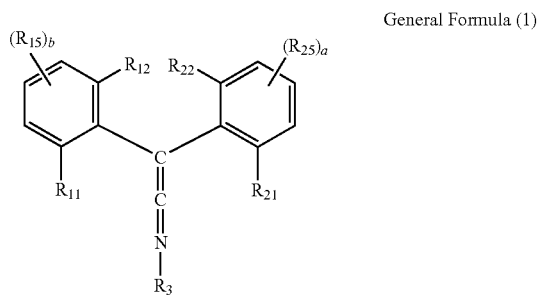

Here, in Formula (1), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent, and $R_{15}$ and $R_{25}$ each independently represent an alkyl group which may have a substituent, an aryl group which may have a substituent, an alkoxy group which may have a substituent, or an aryloxy group which may have a substituent. Moreover, $R_{11}$, $R_{12}$, or $R_{15}$ may form a condensed ring by the substituents adjacent to each other, and $R_{21}$, $R_{22}$, or $R_{25}$ may form a condensed ring by the substituents adjacent to each other. $R_3$ represents an alkyl group which may have a substituent or an aryl group which may have a substituent. In addition, a and b each independently represent an integer of 0 to 3.

The alkyl group moiety of the alkyl group which may have a substituent represented by $R_{11}$, $R_{12}$, $R_{21}$, or $R_{22}$ has preferably 1 to 20 carbon atoms, more preferably 1 to 12 carbon atoms, and still more preferably 1 to 6 carbon atoms. The alkyl group represented by $R_{11}$, $R_{12}$, $R_{21}$, or $R_{22}$ may be a linear alkyl group, a branched alkyl group, or a cyclic alkyl group. Examples of the alkyl group represented by $R_{11}$, $R_{12}$, $R_{21}$, or $R_{22}$ include a methyl group, an ethyl group, an n-propyl group, an iso-propyl group, an n-butyl group, a tert-butyl group, a sec-butyl group, and an iso-butyl group. Among these, a methyl group, an ethyl group, an n-propyl group, and an iso-propyl group are more preferable.

In a case where $R_{11}$, $R_{12}$, $R_{21}$, or $R_{22}$ has a substituent, the substituent is not particularly limited as long as the reactivity between a ketene imine group and a carboxyl group is not excessively reduced. Examples of the substituent include the same substituents as the above-described substituents.

The aryl group moiety of the aryl group which may have a substituent represented by $R_{11}$, $R_{12}$, $R_{21}$, or $R_{22}$ has preferably 6 to 20 carbon atoms, and more preferably 6 to 12 carbon atoms. Examples of the aryl group represented by $R_{11}$, $R_{12}$, $R_{21}$, or $R_{22}$ include a phenyl group, a naphthyl group, and the like, and among these, the phenyl group is particularly preferable. In a case where $R_{11}$, $R_{12}$, $R_{21}$, or $R_{22}$ has a substituent, examples of the substituent include the same substituents as the above-described substituents.

The aryl group includes a heteroaryl group. The heteroaryl group refers to a group obtained by substitution of at least one of ring-constituting atoms of a five-, six-, or seven-membered ring exhibiting aromaticity or the condensed ring thereof with a hetero atom. Examples of the heteroaryl group include an imidazolyl group, a pyridyl group, a quinolyl group, a furyl group, a thienyl group, a benzoxazolyl group, an indolyl group, a benzimidazolyl group, a benzothiazolyl group, a carbazolyl group, and an azepinyl group. The hetero atom included in the heteroaryl group is preferably an oxygen atom, a sulfur atom, or a nitrogen atom, and among these, an oxygen atom or a nitrogen atom is preferable.

The heteroaryl group represented by $R_{11}$, $R_{12}$, $R_{21}$, or $R_{22}$ may further have a substituent, and the substituent is not particularly limited as long as the reactivity between a ketene imine group and a carboxyl group is not excessively reduced.

The alkoxy group moiety of the alkoxy group which may have a substituent represented by $R_{11}$, $R_{12}$, $R_{21}$, or $R_{22}$ has preferably 1 to 20 carbon atoms, more preferably 1 to 12 film including the ketene imine compound. This is because, when $R_{11}$, $R_{12}$, $R_{21}$, or $R_{22}$ has a substituent as described above, a steric hindrance group is introduced into the vicinity of a ketene imine moiety, and due to this, in the polyester resin composition or the polyester film, dimerization of the ketene imine compounds is suppressed. The dimerization of the ketene imine compounds can be suppressed by introducing a steric hindrance group into an ortho position when viewed from the bonding position of $R_{11}$, $R_{12}$, $R_{21}$ or $R_{22}$.

The structure of the dimerization product of the ketene imine compounds is suggested, for example, in Tetrahedron Vol. 49, 6285 (1993). Here, it is shown that the ketene imine compounds are dimerized in the following manner by electro-oxidation, and it is described clearly that the dimer absorbs at even 400 nm or greater (yellow).

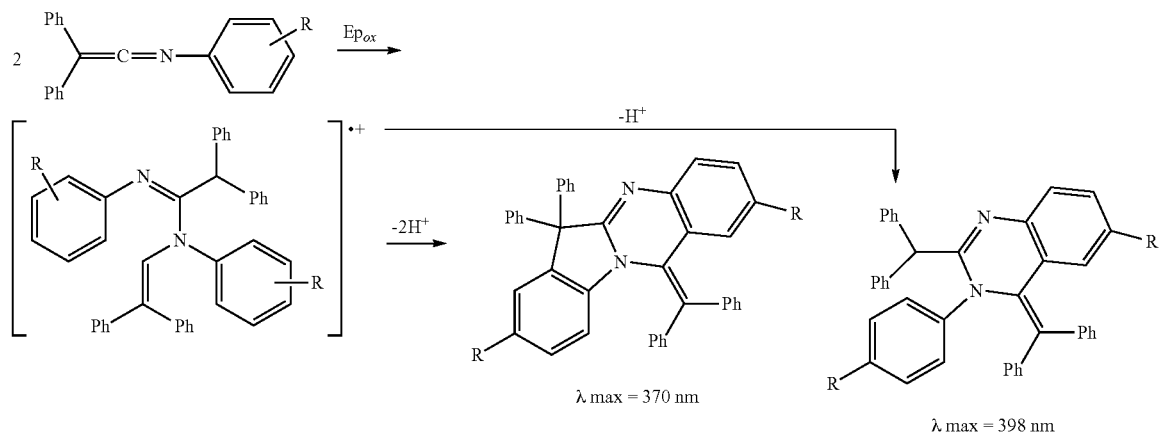

carbon atoms, and still more preferably 1 to 6 carbon atoms. The alkoxy group represented by $R_{11}$, $R_{12}$, $R_{21}$, or $R_{22}$ may be a linear alkoxy group, a branched alkoxy group, or a cyclic alkoxy group. Preferable examples of the alkoxy group represented by $R_{11}$, $R_{12}$, $R_{21}$, or $R_{22}$ include a group in which —O— is linked to the terminal of the above-described alkyl group represented by $R_{11}$, $R_{12}$, $R_{21}$, or $R_{22}$. In a case where $R_{11}$, $R_{12}$, $R_{21}$, or $R_{22}$ has a substituent, examples of the substituent include the same substituents as the above-described substituents.

The aryloxy group moiety of the aryloxy group which may have a substituent represented by $R_{11}$, $R_{12}$, $R_{21}$, or $R_{22}$ has preferably 6 to 20 carbon atoms, and more preferably 6 to 12 carbon atoms. As the aryl moiety of the arylxoy group represented by $R_{11}$, $R_{12}$, $R_{21}$, or $R_{22}$, the aryl group described above can be exemplified.

In Formula (1), each of $R_{11}$, $R_{12}$, $R_{21}$, and $R_{22}$ is preferably an alkoxy group which may have a substituent or an aryloxy group which may have a substituent, more preferably an alkoxy group which may have a substituent, and particularly preferably an alkoxy group which does not have a hydrogen atom at the β-position of the oxygen atom in an alkoxy group. Preferable examples of $R_{11}$, $R_{12}$, $R_{21}$, or $R_{22}$ include a methoxy group and a t-butyl methoxy group, and the most preferable example is a methoxy group.

In the present invention, as described above, when $R_{11}$, $R_{12}$, $R_{21}$, or $R_{22}$ of a ketene imine compound has a substituent, it is possible to suppress yellowing of a polyester In the present invention, at least any one of $R_{11}$ or $R_{12}$, and at least any one of $R_{21}$ or $R_{22}$ are preferably the substituents as described above. That is, the two phenyl groups which are connected to the ketene imine moiety preferably have substituents. In this case, the substituent is preferably an alkoxy group which may have a substituent or an aryloxy group which may have a substituent, more preferably an alkoxy group which may have a substituent, and particularly preferably an alkoxy group which does not have a hydrogen atom at the β-position of the oxygen atom in an alkoxy group. In this manner, when the two phenyl groups which are connected to the ketene imine moiety have steric hindrance groups, it is possible to more effectively suppress the dimerization of ketene imine compounds, and it is possible to suppress yellowing of the polyester film including the ketene imine compound.

In Formula (1), $R_{15}$ and $R_{25}$ each independently represent an alkyl group which may have a substituent, an aryl group which may have a substituent, an alkoxy group which may have a substituent, or an aryloxy group which may have a substituent. Moreover, the substituent represented by $R_{15}$ or $R_{25}$ is the same as that in $R_{11}$, $R_{12}$, $R_{21}$, or $R_{22}$, and the preferable range thereof is also the same.

$R_{11}$, $R_{12}$, or $R_{15}$ may form a condensed ring by the substituents adjacent to each other, and $R_{21}$, $R_{22}$, or $R_{25}$ may form a condensed ring by the substituents adjacent to each other. The condensed ring which $R_{11}$, $R_{12}$, or $R_{15}$ forms by the substituents adjacent to each other and the condensed ring which $R_{21}$, $R_{22}$, or $R_{25}$ forms by the substituents adjacent to each other may be condensed rings of benzene rings, or may be condensed rings of a benzene ring and an aliphatic ring, a benzene ring and a hetero ring, and a benzene ring, an aliphatic ring, and a hetero ring. Among these, a condensed ring formed of benzene rings is preferable.

$R_3$ represents an alkyl group which may have a substituent or an aryl group which may have a substituent. The alkyl group moiety of the alkyl group which may have a substituent represented by $R_3$ has preferably 1 to 20 carbon atoms, more preferably 1 to 12 carbon atoms, and still more preferably 1 to 6 carbon atoms. The alkyl group represented by $R_3$ may be a linear alkyl group, a branched alkyl group, or a cyclic alkyl group. Examples of the alkyl group which is represented by $R_3$ can include a methyl group, an ethyl group, an n-propyl group, an iso-propyl group, an n-butyl group, a tert-butyl group, a sec-butyl group, an iso-butyl group, an n-pentyl group, a sec-pentyl group, an iso-pentyl group, an n-hexyl group, a sec-hexyl group, an iso-hexyl group, and a cyclohexyl group. Among these, a methyl group, an ethyl group, an n-propyl group, an iso-propyl group, an n-butyl group, an iso-butyl group, and a cyclohexyl group are more preferable.

In a case where $R_3$ has a substituent, the substituent is not particularly limited as long as the reactivity between a ketene imine group and a carboxyl group is not reduced. Examples of the substituent can include the same substituents as the above-described substituents.

The aryl group moiety of the aryl group which may have a substituent represented by $R_3$ has preferably 1 to 20 carbon atoms, more preferably 1 to 12 carbon atoms, and still more preferably 1 to 6 carbon atoms. Examples of the aryl group represented by $R_3$ can include a phenyl group and a naphthyl group, and among these, the phenyl group is particularly preferable. In a case where $R_3$ has a substituent, examples of the substituent can include the same substituents as the above-described substituents.

The aryl group includes a heteroaryl group. The heteroaryl group refers to a group obtained by substitution of at least one of ring-constituting atoms of a five-, six-, or seven-membered ring exhibiting aromaticity or the condensed ring thereof with a hetero atom. Examples of the heteroaryl group include an imidazolyl group, a pyridyl group, a quinolyl group, a furyl group, a thienyl group, a benzoxazolyl group, an indolyl group, a benzimidazolyl group, a benzothiazolyl group, a carbazolyl group, and an azepinyl group. The hetero atom included in the heteroaryl group is preferably an oxygen atom, a sulfur atom, or a nitrogen atom, and among these, an oxygen atom or a nitrogen atom is preferable.

In Formula (1), a and b each independently represent an integer of 0 to 3. a and b each independently preferably represent an integer of 0 to 2, and more preferably represent an integer of 0 or 1.

Moreover, Formula (1) may include a repeating unit. In this case, a ketene imine moiety is preferably included in the repeating unit.

In addition, the ketene imine compound used in the present invention is preferably the compound which is represented by the following Formula (2).

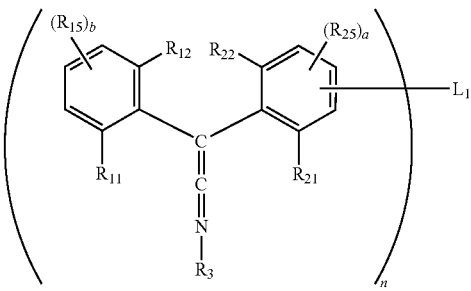

General Formula (2)

Here, in Formula (2), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent, and $R_{15}$ and $R_{25}$ each independently represent an alkyl group which may have a substituent, an aryl group which may have a substituent, an alkoxy group which may have a substituent, or an aryloxy group which may have a substituent. Moreover, $R_{11}$, $R_{12}$, or $R_{15}$ may form a condensed ring by the substituents adjacent to each other, and $R_{21}$, $R_{22}$, or $R_{25}$ may form a condensed ring by the substituents adjacent to each other. $R_3$ represents an alkyl group which may have a substituent or an aryl group which may have a substituent. In addition, a represents an integer of 0 to 2, and b represents an integer of 0 to 3. n represents an integer of 1 to 4, and $L_1$ represents an n valent linking group.

In Formula (2), $R_{11}$, $R_{12}$, $R_{21}$, and $R_{22}$ have the same meaning as those in Formula (1), and the preferable ranges thereof are also the same.

In addition, in Formula (2), $R_{15}$ and $R_{25}$ have the same meaning as those in Formula (1), and the preferable ranges thereof are also the same.

In Formula (2), the condensed ring which $R_{11}$, $R_{12}$, or $R_{15}$ forms by the substituents adjacent to each other and the condensed ring which $R_{21}$, $R_{22}$, or $R_{25}$ forms by the substituents adjacent to each other have the same meaning as those in Formula (1), and the preferable ranges thereof are also the same.

In Formula (2), $R_3$ has the same meaning as that in Formula (1), and the preferable range thereof is also the same.

In Formula (2), a represents an integer of 0 to 2, and b represents an integer of 0 to 3. a preferably represents an integer of 0 or 1, and b preferably represents an integer of 0 to 2, and more preferably represents an integer of 0 or 1.

In Formula (2), $L_1$ represents an n valent linking group, and n represents an integer of 1 to 4. Among these, n is preferably 2 to 4, and more preferably 3 or 4.

Specific examples of the divalent linking group include a group which is represented by —$NR_8$— ($R_8$ represents a hydrogen atom, an alkyl group which may have a substituent, or an aryl group which may have a substituent, and a hydrogen atom is preferable), —$SO_2$—, —CO—, a substituted or unsubstituted alkylene group, a substituted or unsubstituted alkenylene group, alkynylene group, a substituted or unsubstituted phenylene group, a substituted or unsubstituted biphenylene group, a substituted or unsubstituted naphthylene group, —O—, —S—, —SO—, and a group obtained by combining two or more thereof.

Specific examples of the trivalent linking group include a group obtained by removing one hydrogen atom from a group having a substituent among the linking groups exemplified as the divalent linking group.

Specific examples of the tetravalent linking group include a group obtained by removing two hydrogen atoms from a group having a substituent among the linking groups exemplified as the divalent linking group.

In the present invention, when n is any one of 2 to 4, a compound having two or more ketene imine moieties in one molecule can be obtained, and a further improved terminal blocking effect can be exhibited. In addition, when a compound has two or more ketene imine moieties in one molecule, it is possible to increase the molecular weight of the ketene imine compound, and it is possible to suppress volatilization of the ketene imine compound or the ketene compound. Furthermore, when a compound has two or more ketene imine moieties in one molecule, it is possible to reduce the ketene imine value (the total molecular weight/the number of functional groups of ketene imine), and it is possible to efficiently react the ketene imine compound with a terminal carboxyl group of polyester.

In Formula (2), n is more preferably 3 or 4. When n is 3 or 4, a compound having three or four ketene imine moieties in one molecule can be obtained, and a further improved terminal blocking effect can be exhibited. In addition, when n is 3 or 4, it is possible to more effectively suppress volatilization of the ketene imine compound.

The ketene imine compound used in the present invention is preferably a compound represented by the following Formula (3-1).

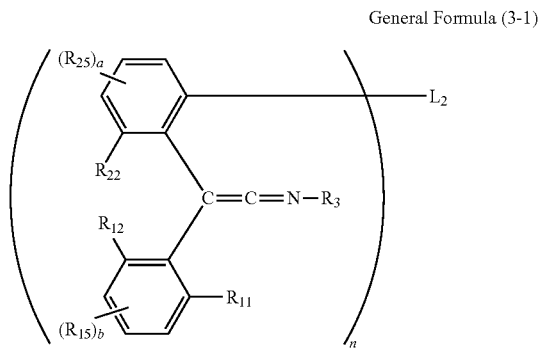

General Formula (3-1)

Here, in Formula (3-1), at least one of $R_{11}$, $R_{12}$, and $R_{22}$ each independently represents an alkyl group which may have a substituent, an aryl group which may have a substituent, an alkoxy group which may have a substituent, or an aryloxy group which may have a substituent, and $R_{15}$ and $R_{25}$ each independently represent an alkyl group which may have a substituent, an aryl group which may have a substituent, an alkoxy group which may have a substituent, or an aryloxy group which may have a substituent. Moreover, $R_{11}$, $R_{12}$, or $R_{15}$ may form a condensed ring by the substituents adjacent to each other, and $R_{22}$ and $R_{25}$ may form a condensed ring by the substituents adjacent to each other. $R_3$ represents an alkyl group which may have a substituent or an aryl group which may have a substituent. In addition, a and b each independently represent an integer of 0 to 3. n represents an integer of 1 to 4, and $L_2$ represents an n valent linking group.

In Formula (3-1), $R_{11}$, $R_{12}$, and $R_{22}$ have the same meaning as those in Formula (1), and the preferable ranges thereof are also the same.

In addition, in Formula (3-1), $R_{15}$ and $R_{25}$ have the same meaning as those in Formula (1), and the preferable ranges thereof are also the same.

In Formula (3-1), the condensed ring which $R_{11}$, $R_{12}$, or $R_{15}$ forms by the substituents adjacent to each other and the condensed ring which $R_{22}$ or $R_{25}$ forms by the substituents adjacent to each other have the same meaning as those in Formula (1), and the preferable ranges thereof are also the same.

In Formula (3-1), $R_3$ has the same meaning as that in Formula (1), and the preferable range thereof is also the same.

In Formula (3-1), a and b each independently represent an integer of 0 to 3. a and b each independently preferably represent an integer of 0 to 2, and more preferably represent an integer of 0 or 1.

In Formula (3-1), $L_2$ represents an n valent linking group, and here, n represents an integer of 1 to 4. Among these, n is preferably 2 to 4, and more preferably 3 or 4.

Specific examples of the $L_2$ linking group can include linking groups exemplified as $L_1$ in Formula (2).

The ketene imine compound used in the present invention is preferably a compound represented by the following Formula (3-2).

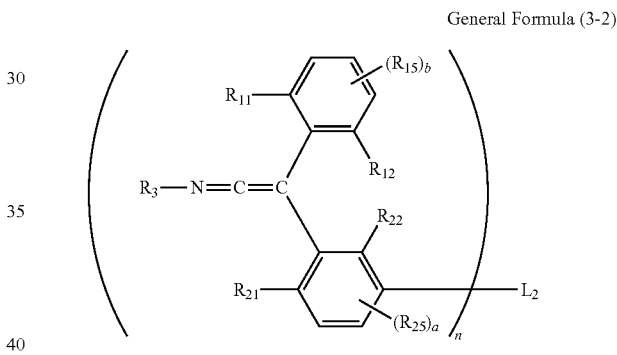

General Formula (3-2)

Here, in Formula (3-2), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent, and $R_{15}$ and $R_{25}$ each independently represent an alkyl group which may have a substituent, an aryl group which may have a substituent, an alkoxy group which may have a substituent, or an aryloxy group which may have a substituent. Moreover, $R_{11}$, $R_{12}$, or $R_{15}$ may form a condensed ring by the substituents adjacent to each other, and $R_{21}$ and $R_{25}$ may form a condensed ring by the substituents adjacent to each other. $R_3$ represents an alkyl group which may have a substituent or an aryl group which may have a substituent. In addition, a represents an integer of 0 to 2, and b represents an integer of 0 to 3. n represents an integer of 1 to 4, and $L_1$ represents an n valent linking group.

In Formula (3-2), $R_{11}$, $R_{12}$, $R_{21}$, and $R_{22}$ have the same meaning as those in Formula (1), and the preferable ranges thereof are also the same.

In addition, in Formula (3-2), $R_{15}$ and $R_{25}$ have the same meaning as those in Formula (1), and the preferable ranges thereof are also the same.

In Formula (3-2), the condensed ring which $R_{11}$, $R_{12}$, or $R_{15}$ forms by the substituents adjacent to each other and the condensed ring which $R_{21}$ or $R_{25}$ forms by the substituents adjacent to each other have the same meaning as those in Formula (1), and the preferable ranges thereof are also the same.

In Formula (3-2), $R_3$ has the same meaning as that in Formula (1), and the preferable range thereof is also the same.

In Formula (3-2), a represents an integer of 0 to 2, and b represents an integer of 0 to 3. a preferably represents an integer of 0 or 1. In addition, b preferably represents an integer of 0 to 2, and more preferably represents an integer of 0 or 1.

In Formula (3-2), $L_2$ represents an n valent linking group, and here, n represents an integer of 1 to 4. Among these, n is preferably 2 to 4, and more preferably 3 or 4. Specific examples of the $L_2$ linking group can include linking groups exemplified as $L_1$ in Formula (2).

The ketene imine compound used in the present invention is a compound represented by the following Formula (4).

General Formula (4)

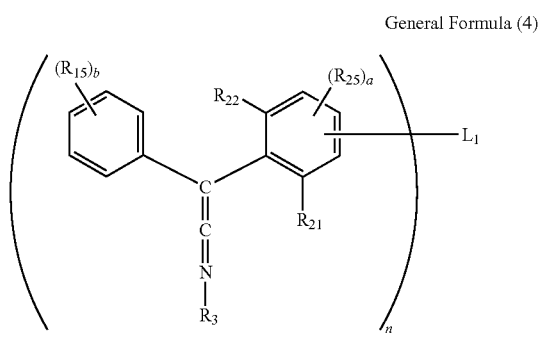

Here, in Formula (4), at least one of $R_{21}$ and $R_{22}$ each independently represents an alkyl group which may have a substituent, an aryl group which may have a substituent, an alkoxy group which may have a substituent, or an aryloxy group which may have a substituent. $R_{15}$ and $R_{25}$ each independently represent an alkyl group which may have a substituent, an aryl group which may have a substituent, an alkoxy group which may have a substituent, or an aryloxy group which may have a substituent. Moreover, $R_{15}$ may form a condensed ring by the substituents adjacent to each other, and $R_{21}$, $R_{22}$, or $R_{25}$ may form a condensed ring by the substituents adjacent to each other. $R_3$ represents an alkyl group which may have a substituent or an aryl group which may have a substituent. In addition, a represents an integer of 0 to 2, and b represents an integer of 0 to 5. n represents an integer of 1 to 4, and $L_1$ represents an n valent linking group.

In Formula (4), $R_{21}$ and $R_{22}$ have the same meaning as those in Formula (1), and the preferable ranges thereof are also the same.

In addition, in Formula (4), $R_{15}$ and $R_{25}$ have the same meaning as those in Formula (1), and the preferable ranges thereof are also the same.

In Formula (4), the condensed ring which $R_{15}$ forms by the substituents adjacent to each other and the condensed ring which $R_{21}$, $R_{22}$, or $R_{25}$ forms by the substituents adjacent to each other have the same meaning as those in Formula (1), and the preferable ranges thereof are also the same.

In Formula (4), $R_3$ has the same meaning as that in Formula (1), and the preferable range thereof is also the same.

In Formula (4), a represents an integer of 0 to 2, and b represents an integer of 0 to 5. a preferably represents an integer of 0 or 1. In addition, b preferably represents an integer of 0 to 3, more preferably represents an integer of 0 to 2, and still more preferably represents an integer of 0 or 1.

In Formula (4), $L_1$ represents an n valent linking group, and n represents an integer of 1 to 4. Among these, n is preferably 2 to 4, and more preferably 3 or 4. Specific examples of the $L_1$ linking group can include linking groups exemplified as $L_1$ in Formula (2).

At least one of $R_{21}$ and $R_{22}$ in Formula (4) is preferably an alkoxy group which may have a substituent, and an aryloxy group which may have a substituent. Furthermore, $R_{22}$ in Formula (4) is more preferably an alkoxy group which may have a substituent, and an aryloxy group which may have a substituent.

The ketene imine compound used in the present invention is preferably a compound represented by the following Formula (5).

General Formula (5)

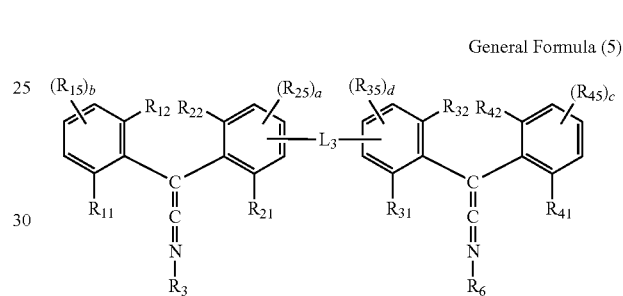

Here, in Formula (5), at least one of $R_{11}$, $R_{12}$, $R_{21}$, $R_{22}$, $R_{31}$, $R_{32}$, $R_{41}$, and $R_{42}$ each independently represents an alkyl group which may have a substituent, an aryl group which may have a substituent, an alkoxy group which may have a substituent, or an aryloxy group which may have a substituent. $R_{15}$, $R_{25}$, $R_{35}$, and $R_{45}$ each independently represent an alkyl group which may have a substituent, an aryl group which may have a substituent, an alkoxy group which may have a substituent, or an aryloxy group which may have a substituent. Moreover, $R_{11}$, $R_{12}$, or $R_{15}$ may form a condensed ring by the substituents adjacent to each other, $R_{21}$, $R_{22}$ or $R_{25}$ may form a condensed ring by the substituents adjacent to each other, $R_{31}$, $R_{32}$, or $R_{35}$ may form a condensed ring by the substituents adjacent to each other, and $R_{41}$, $R_{42}$, or $R_{45}$ may form a condensed ring by the substituents adjacent to each other. $R_3$ and $R_6$ each represent an alkyl group which may have a substituent or an aryl group which may have a substituent. In addition, a and b each independently represent an integer of 0 to 2, and b and c each independently represent an integer of 0 to 3. $L_3$ represents a single bond or a divalent linking group.

In Formula (5), $R_{11}$, $R_{12}$, $R_{21}$, $R_{22}$, $R_{31}$, $R_{32}$, $R_{41}$, and $R_{42}$ have the same meaning as $R_{11}$, $R_{12}$, $R_{21}$, or $R_{22}$ in Formula (1), and the preferable ranges thereof are also the same.

In addition, in Formula (5), $R_{15}$, $R_{25}$, $R_{35}$, and $R_{45}$ have the same meaning as $R_{15}$ or $R_{25}$ in Formula (1), and the preferable ranges thereof are also the same.

In Formula (5), the condensed ring which $R_{11}$, $R_{12}$, or $R_{15}$ forms by the substituents adjacent to each other, the condensed ring which $R_{21}$, $R_{22}$, or $R_{25}$ forms by the substituents adjacent to each other, the condensed ring which $R_{31}$, $R_{32}$, or $R_{35}$ forms by the substituents adjacent to each other, and the condensed ring which $R_{41}$, $R_{42}$, or $R_{45}$ forms by the substituents adjacent to each other have the same meaning as those in Formula (1), and the preferable ranges thereof are also the same.

In Formula (5), $R_3$ and $R_6$ have the same meaning as $R_3$ in Formula (1), and the preferable ranges thereof are also the same.

In Formula (5), a and d each independently represent an integer of 0 to 2, and b and c each independently represent an integer of 0 to 3. a and d each independently preferably represent an integer of 0 or 1. In addition, b and c each independently preferably represent an integer of 0 or 1, and more preferably represent an integer of 0 or 1.

In Formula (5), $L_3$ represents a single bond or a divalent linking group. Specific examples of the divalent linking group can include linking groups exemplified as $L_1$ in Formula (2).

At least one of $R_{11}$, $R_{12}$, $R_{21}$, $R_{22}$, $R_{31}$, $R_{32}$, $R_{41}$, and $R_{42}$ in Formula (5) preferably represents an alkoxy group which may have a substituent or an aryloxy group which may have a substituent. Furthermore, at least one of $R_{21}$, $R_{22}$, $R_{31}$, and $R_{32}$ preferably represents an alkoxy group which may have a substituent or an aryloxy group which may have a substituent.

A ketene imine compound in which a substituent is introduced into at least one of ortho positions of the two phenyl groups which are connected to the ketene imine moiety as described above can be synthesized by the Friedel-Crafts reaction of a phenol compound with a mandelic acid or a derivative thereof, amidation, phenol protection (introduction of an alkoxy group), and amide dehydration.

The Friedel-Crafts reaction can be performed, in general, by formation of a lactone ring by dehydration condensation using an acid, or by formation of a lactone ring by dehydration condensation by heating. The general synthetic method of the ketene imine compound is as follows.

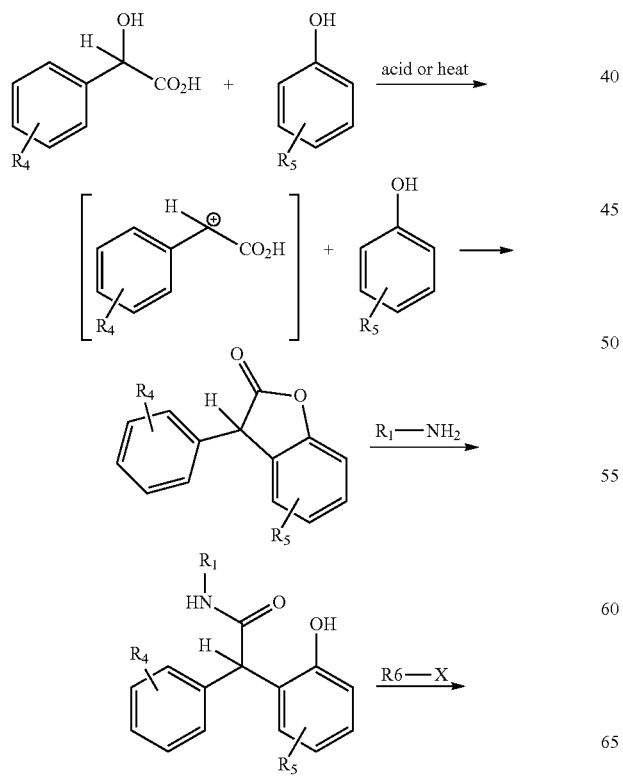

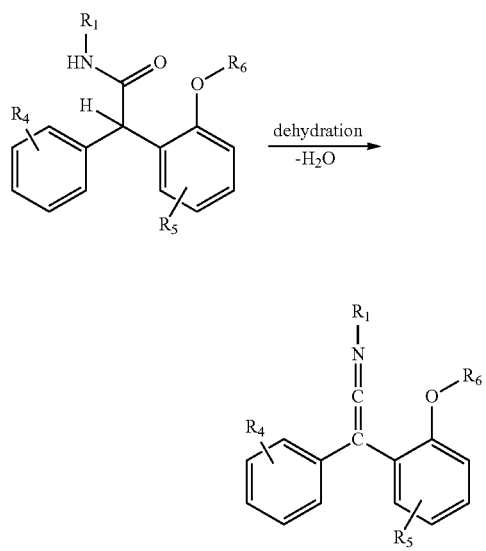

In addition, in the case of synthesizing a ketene imine compound having an n valent linking group, an n valent ketene imine may be obtained by bonding a phenol skeleton with an n valent linking group, but after obtaining ketene imine using an n valent phenol skeleton, an n valent ketene imine compound is preferably obtained. Moreover, a polyphenol mother nucleus is an n valent residue formed by removing n hydroxy groups from an n valent polyphenol. It is essential that a hydrogen atom is at an ortho position of the phenol substituent from the viewpoint of ketene imine introduction. Examples of the n valent polyphenol having a hydrogen atom at an ortho position can include the following Formulas P-1 to P-8. However, the present invention is not limited thereto.

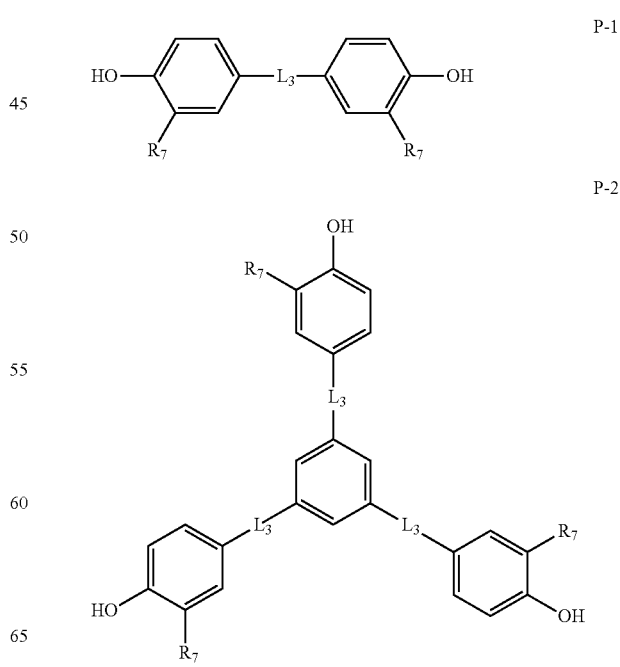

-continued

P-3

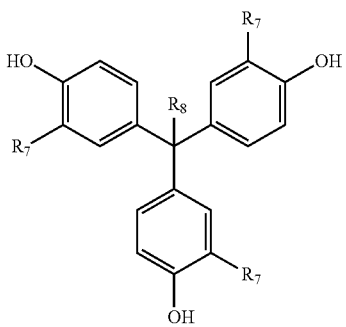

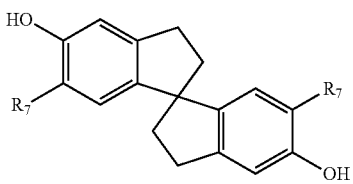

P-4

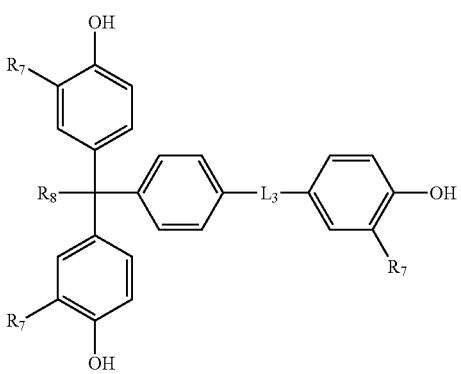

Moreover, in Formulas P-1 to P-8, $R_7$ represents a hydrogen atom, an alkyl group, or an aryl group, $L_3$ represents a single bond, an alkylene group, an oxygen atom, or a sulfur atom, and $R_8$ represents a hydrogen atom, an alkyl group, or an aryl group.

In the present invention, the molecular weight of the ketene imine compound is preferably 500 or greater. The molecular weight of the ketene imine compound is preferably 500 or greater, more preferably 600 or greater, and still more preferably 630 or greater. Examples of the molecular weight include a range of 597 to 1325, a range of 597 to 667, and a range of 639 to 667. In addition, the ketene imine value is preferably 420 or less, more preferably 380 or less, and still more preferably 340 or less. Examples of the ketene imine value include a range of 299 to 376, and a range of 320 to 334. Here, the ketene imine value represents (the total molecular weight/the number of functional groups of ketene imine). In the present invention, when the molecular weight of the ketene imine compound is within the above-described range, it is possible to suppress volatilization of the ketene imine compound. Furthermore, when the ketene imine value is within the above-described range, it is possible to efficiently perform blocking of the terminal carboxyl group of polyester.

P-5

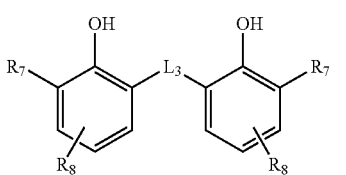

Preferable specific examples of the following Formula (1) are shown below, but the present invention is not limited thereto.

Exemplary Compound (1)

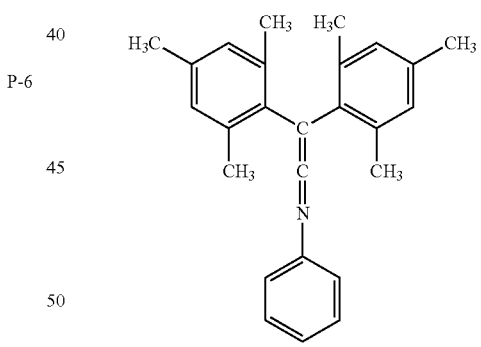

P-6

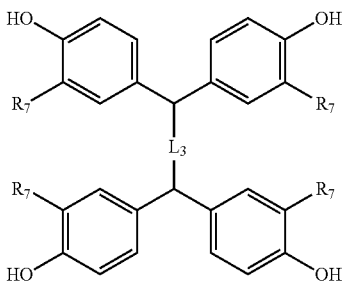

P-7

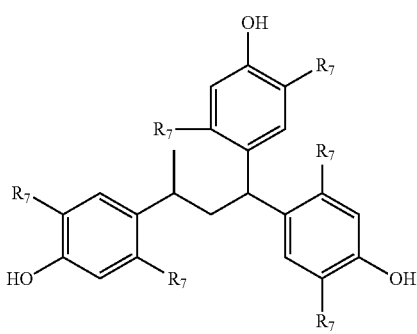

Exemplary Compound (2)

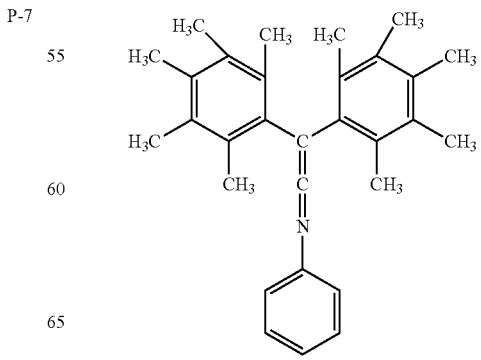

Exemplary Compound (3)
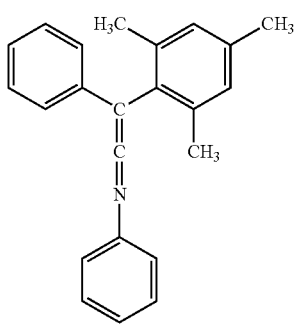
Exemplary Compound (4)
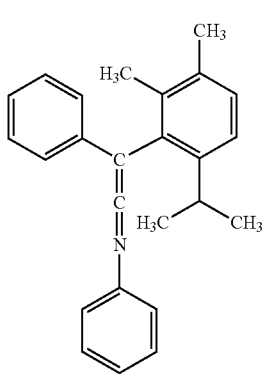
Exemplary Compound (5)
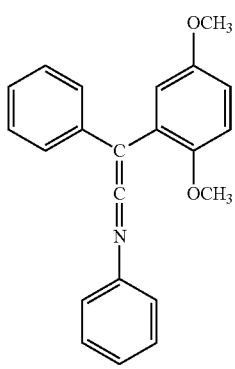
Exemplary Compound (6)
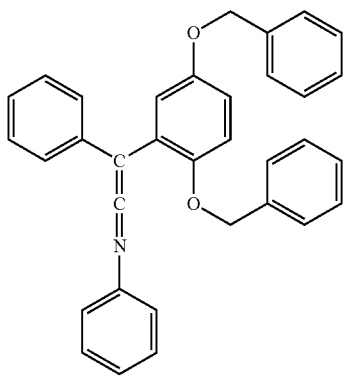
Exemplary Compound (7)
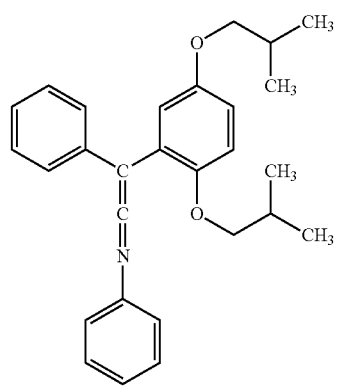
Exemplary Compound (8)
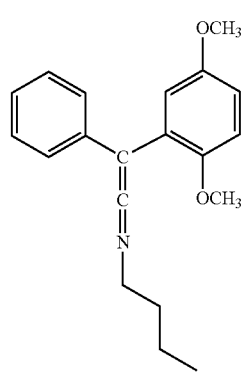
Exemplary Compound (9)
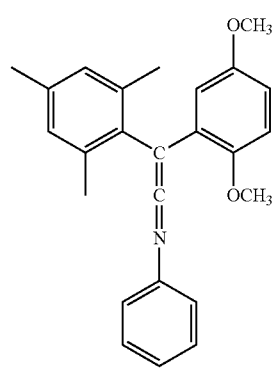
Exemplary Compound (10)
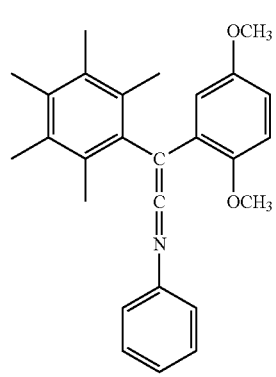

Exemplary Compound (11)
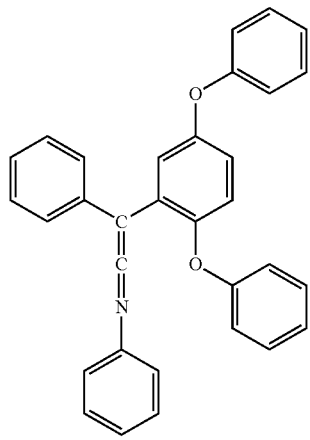
Exemplary Compound (12)
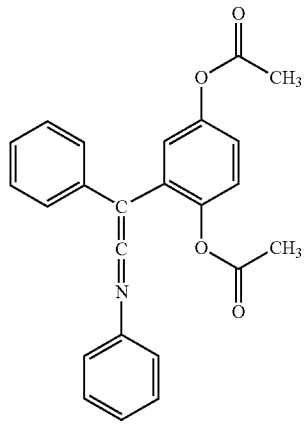
Exemplary Compound (13)
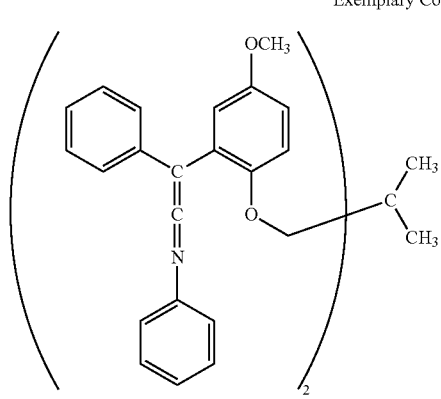
Exemplary Compound (14)
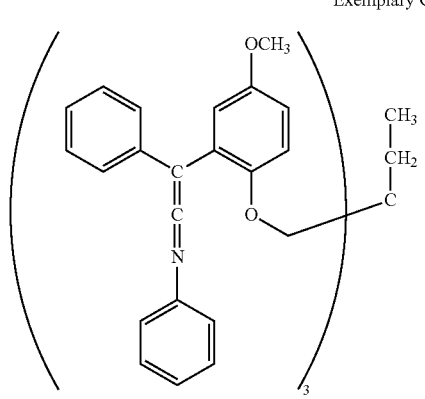
Exemplary Compound (15)
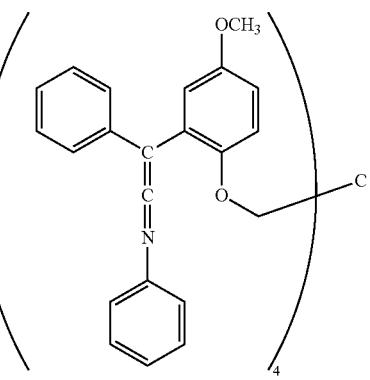
Exemplary Compound (16)
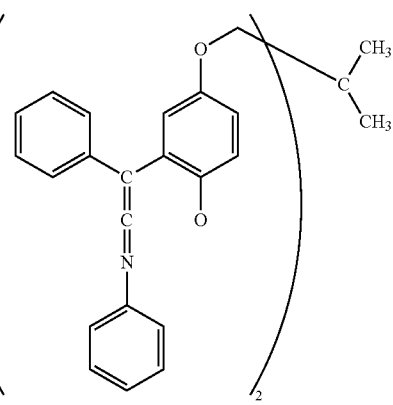
Exemplary Compound (17)
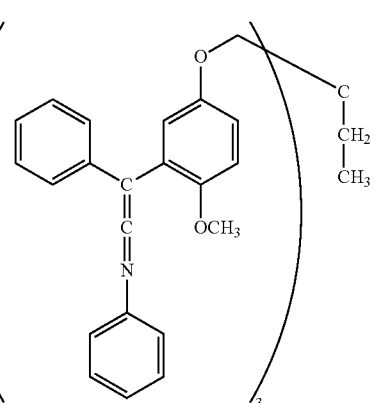
Exemplary Compound (18)
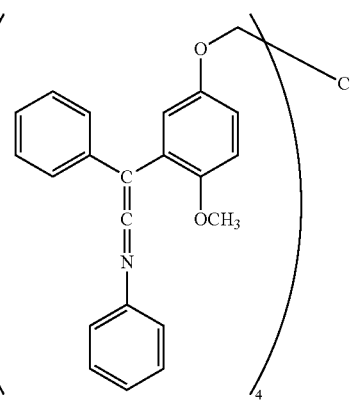

Exemplary Compound (19)
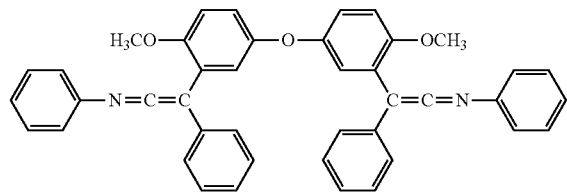
Exemplary Compound (20)
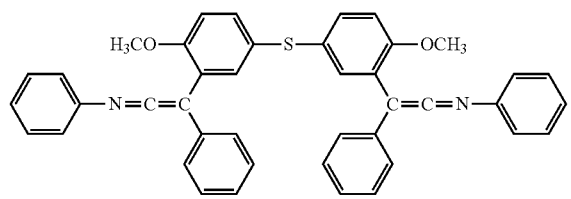
Exemplary Compound (21)
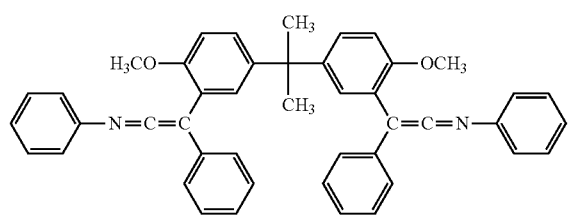
Exemplary Compound (22)
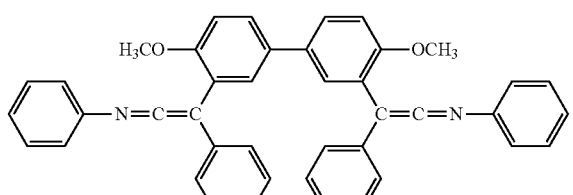
Exemplary Compound (23)
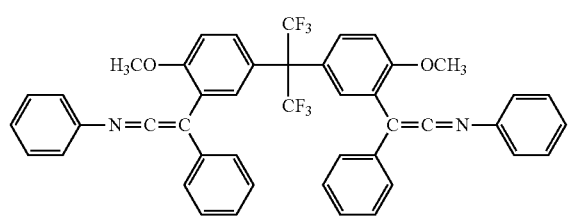
Exemplary Compound (24)
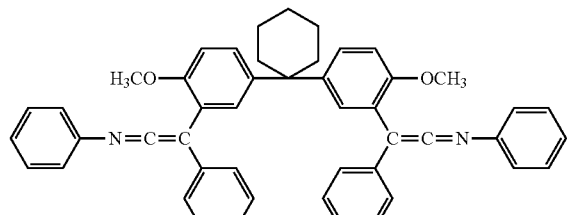
Exemplary Compound (25)
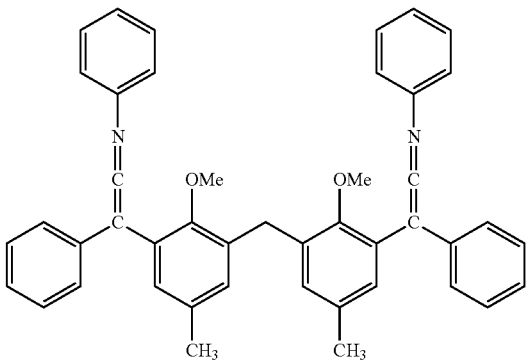
Exemplary Compound (26)
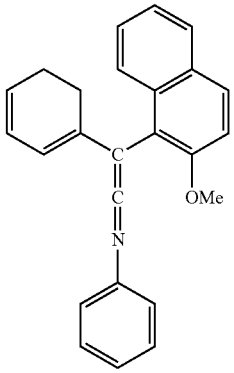
Exemplary Compound (27)
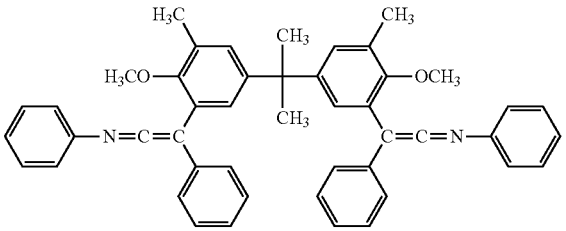
Exemplary Compound (28)
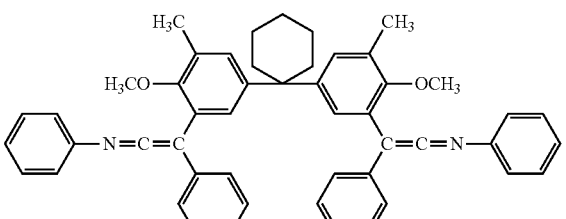
Exemplary Compound (29)
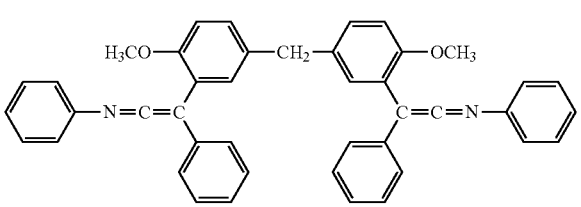

Exemplary Compound (30)
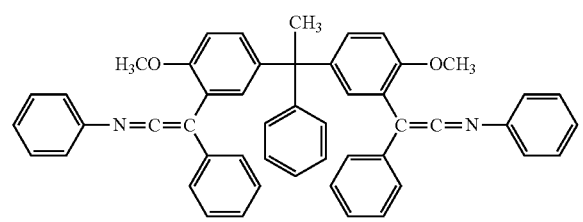
Exemplary Compound (31)
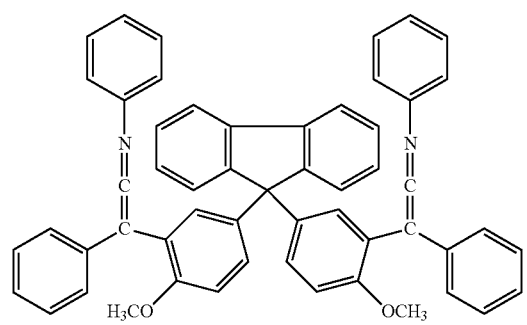
Exemplary Compound (32)
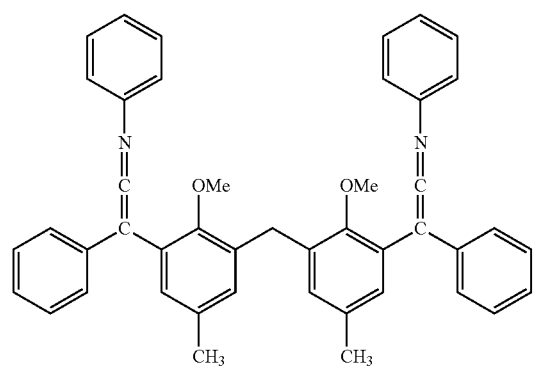
Exemplary Compound (33)
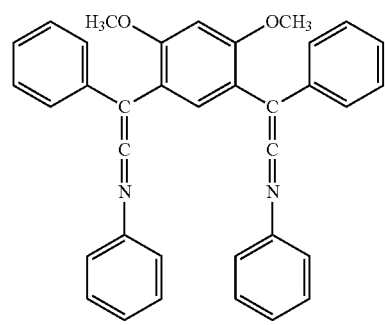
Exemplary Compound (34)
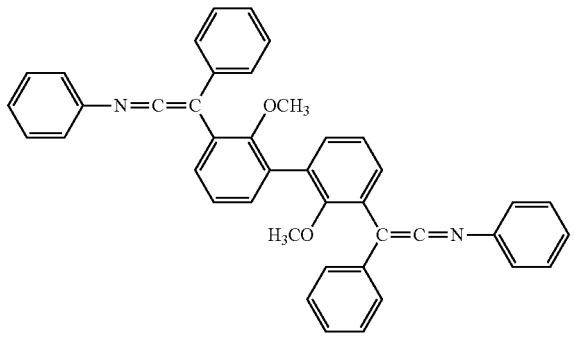
Exemplary Compound (35)
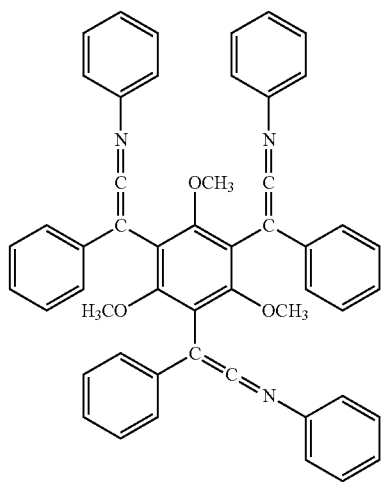
Exemplary Compound (36)
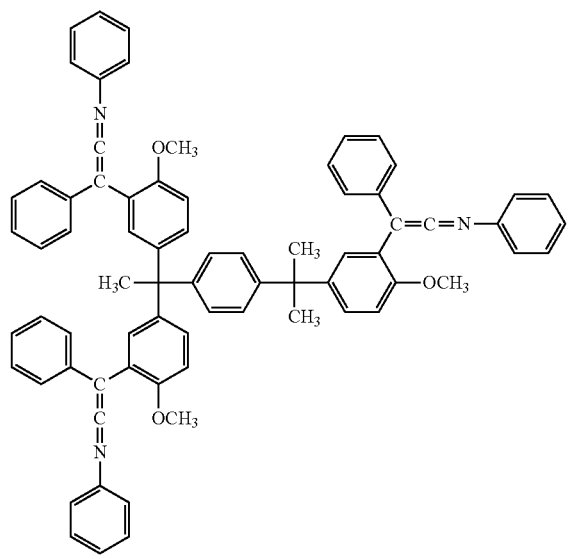

Exemplary Compound (37)
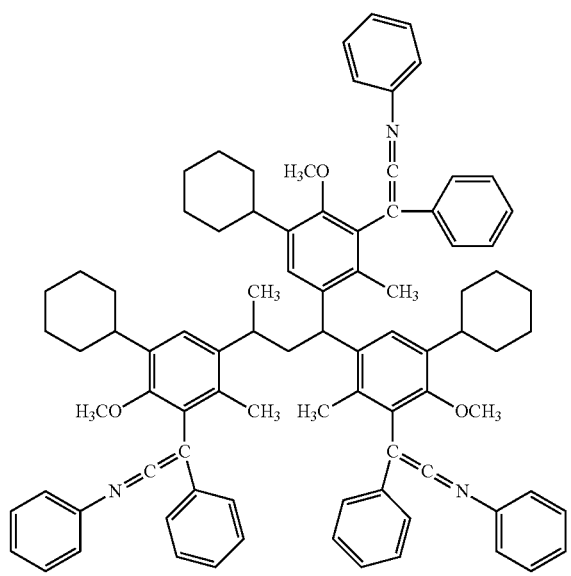
Exemplary Compound (38)
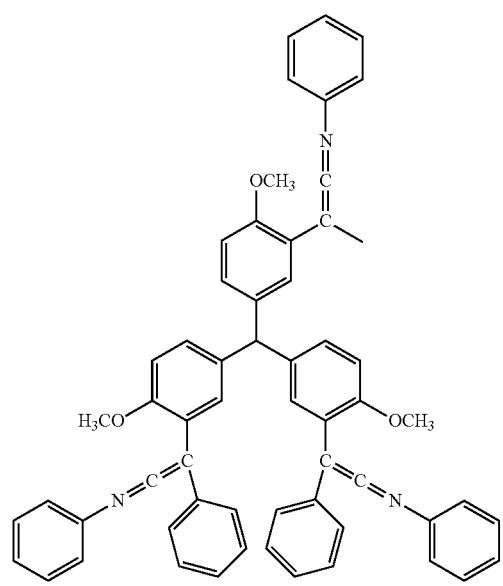
Exemplary Compound (39)
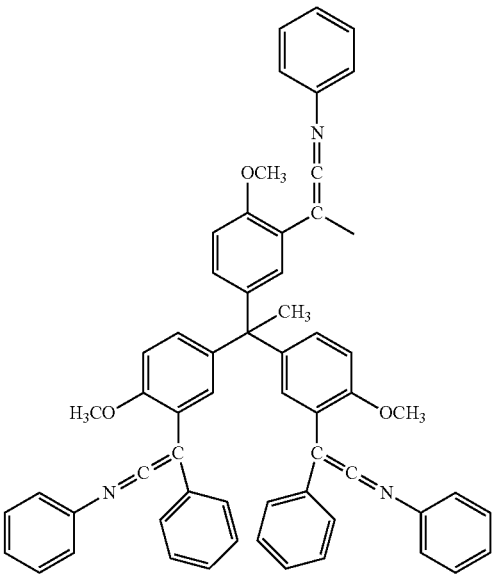
Exemplary Compound (40)
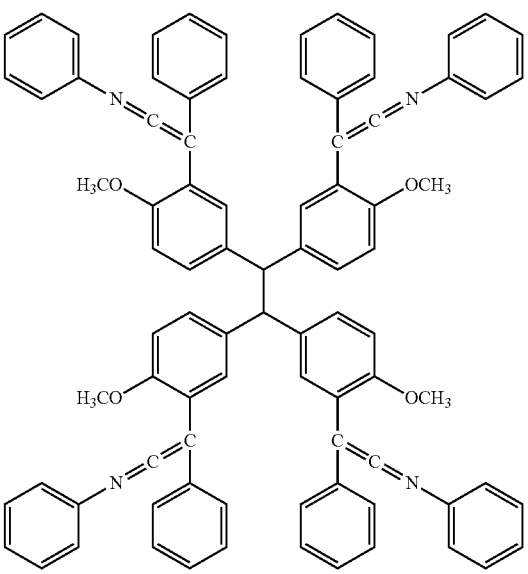
Exemplary Compound (41)
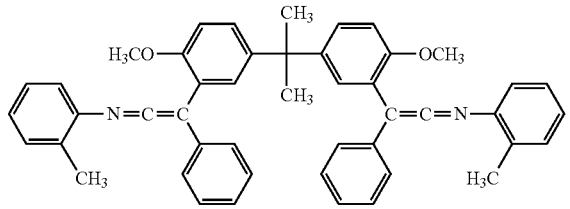
Exemplary Compound (42)
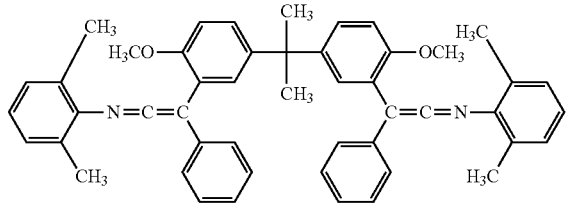

Exemplary Compound (43)
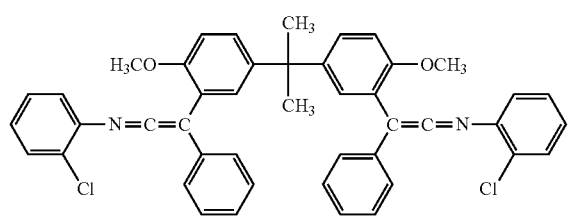
Exemplary Compound (44)
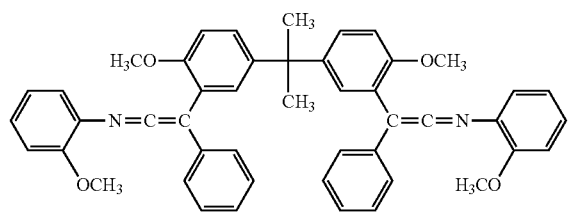
Exemplary Compound (45)
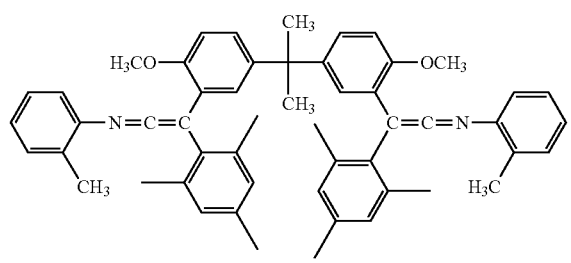
Exemplary Compound (46)
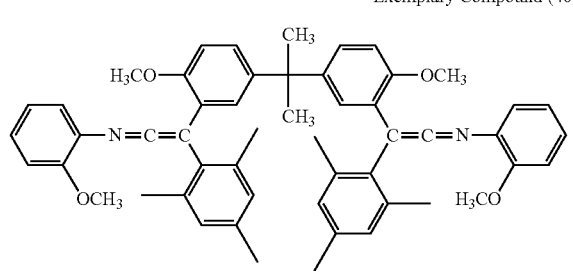
Exemplary Compound (47)
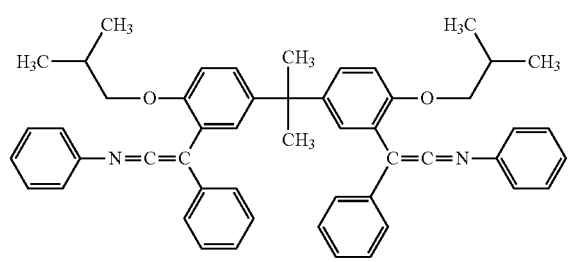
Exemplary Compound (48)
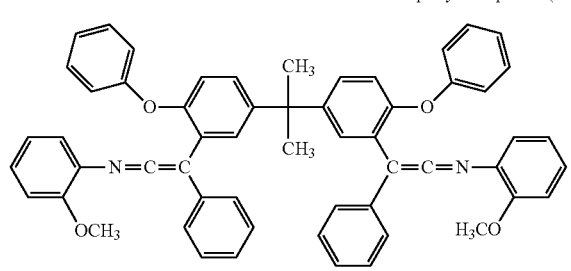
Exemplary Compound (49)
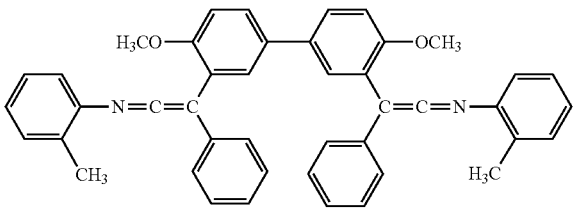
Exemplary Compound (50)
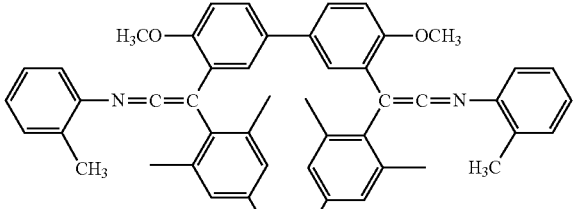
Exemplary Compound (51)
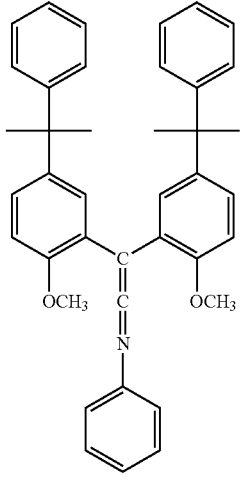
Exemplary Compound (52)
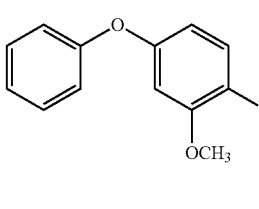

Exemplary Compound (53)
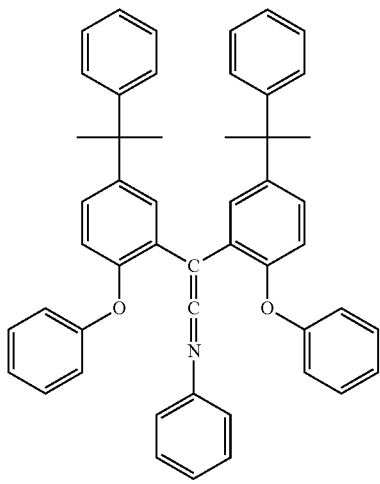
Exemplary Compound (54)
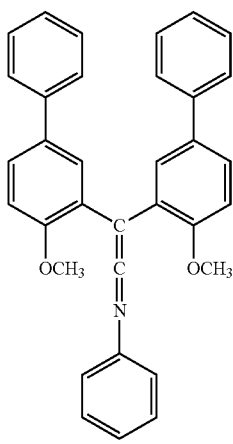
Exemplary Compound (55)
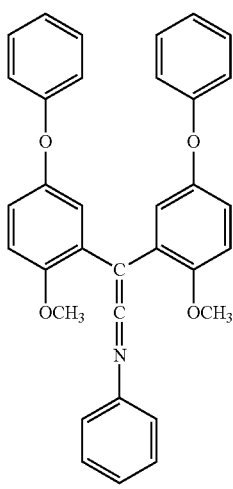
Exemplary Compound (56)
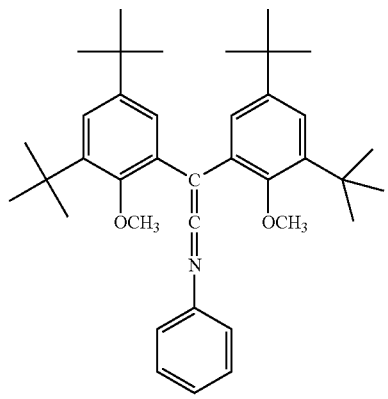
Exemplary Compound (57)
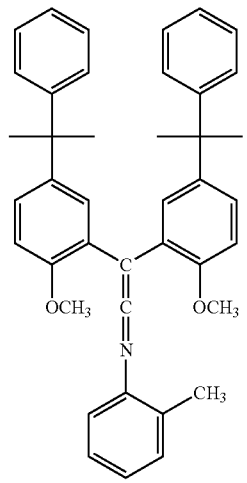
Exemplary Compound (58)
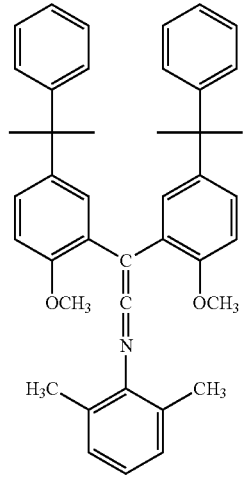

Exemplary Compound (59)

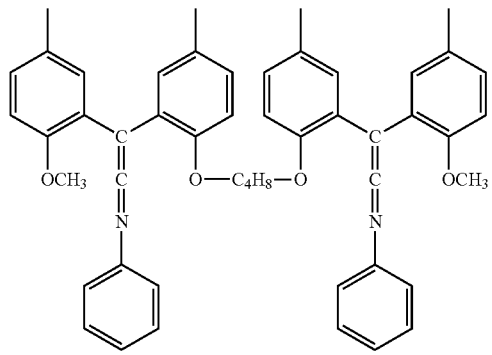

Exemplary Compound (60)

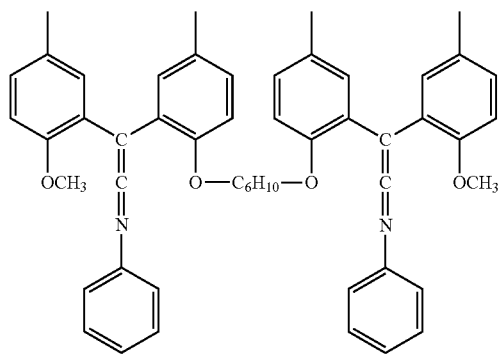

Exemplary Compound (61)

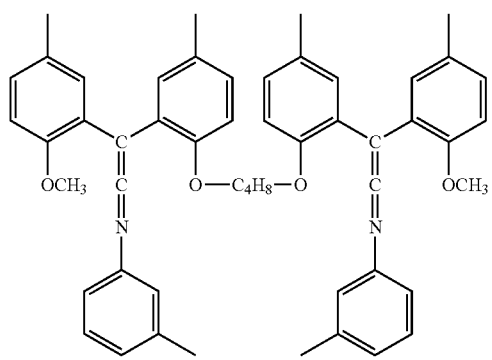

Exemplary Compound (62)

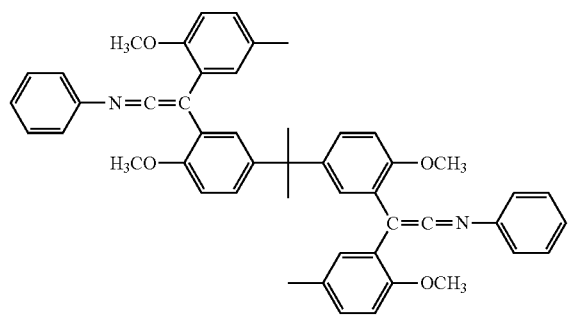

Exemplary Compound (63)

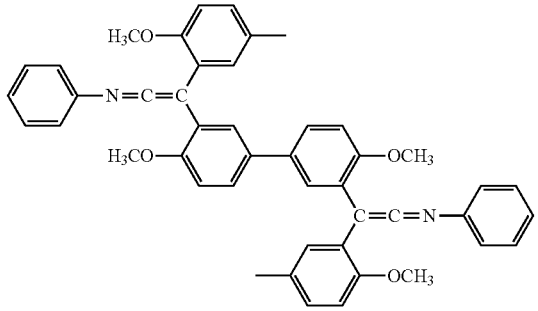

The ketene imine compound used in the present invention is preferably a compound derived from polyphenol. Thus, it is possible to easily synthesize a multifunctional ketene imine compound. For example, Exemplary Compounds 19 to 25, 27 to 50, and 59 to 63 are examples preferable as the ketene imine compound. From the viewpoint of being capable of forming a bifunctional ketene imine compound, Exemplary Compounds 19 to 25, Exemplary Compounds 27 to 34, Exemplary Compounds 41 to 50, and Exemplary Compounds 59 to 63 are more preferable. From the viewpoint of excellent compatibility with a PET film which can be synthesized at a low cost, Exemplary Compound 21, Exemplary Compounds 41 to 48, and Exemplary Compounds 59 to 63 which have a bisphenol A as a basic skeleton are still more preferable. From the viewpoint of being capable of remarkably suppressing production of dimers of the ketene imine compounds which cause yellowing, by a steric effect of a substituent, Exemplary Compound 59 to 63 are particularly preferable.

Chemical modification of a polyester terminal carboxyl group of the present invention can be performed by mixing the ketene imine compound which is represented by Formula (1) and polyester in a melt state.

It is described in Patent Document 1 that the ketene imine compound and polyester are mixed in a melt state, and it is a known method. According to Patent Document 1, in the case of mixing the ketene imine compound and polyester in a melt state, as the following reaction scheme, an imide compound (1) is produced by the reaction of the ketene imine compound with polyester-COOH. By the mechanism, the polyester terminal carboxyl group is blocked.

However, as a result of thorough studies, the present inventors found that the ketene imine compound and the ketene compound (1) volatilize during melt mixing. From this, it can be estimated that the ketene compound (1) and polyester blocked by the terminal amide group are obtained from a portion of the imide compound (1) by heat in the reaction.

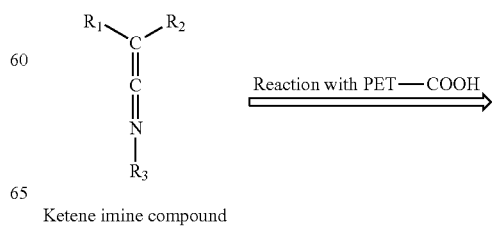

Ketene imine compound

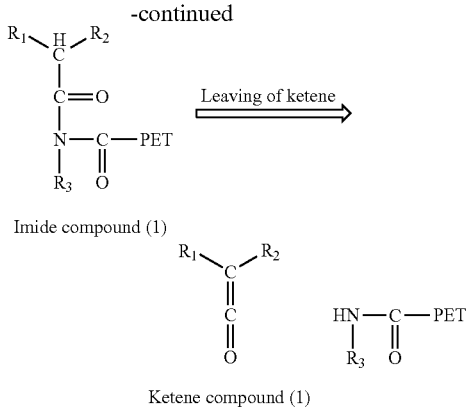

Imide compound (1)

Ketene compound (1)

In the present invention, it is also possible to suppress volatilization of the ketene compound (1) produced by the above-described reaction scheme. When the mass of the ketene imine compound is within a predetermined range, it is possible to suppress volatilization of the ketene imine compound and the ketene compound.

(Polyester Resin Composition)

The polyester resin composition of the present invention includes the ketene imine compound and the polyester as described above. Moreover, within a range not interfering with the effects of the present invention, various additives, for example, a compatibilizer, a plasticizer, a weathering agent, an antioxidant, a thermal stabilizer, a lubricant, an antistatic agent, a brightener, a colorant, a conductive agent, an ultraviolet absorber, a flame retardant, a flame retardant auxiliary agent, a pigment, a dye, or the like may be included in the polyester resin composition of the present invention.

Although the polyester is not particularly limited, the polyester is preferably saturated polyester. By using such saturated polyester, it is possible to obtain an excellent polyester film compared to the film using unsaturated polyester from the viewpoint of dynamic strength.

The polyester has a —COO— bond or a —OCO— bond in a molecular chain of the polymer. In addition, the terminal group of the polyester is preferably a linear saturated polyester synthesized from an aromatic dibasic acid or an derivative for forming an ester thereof, a diol or an derivative for forming an ester thereof as an OH group, a COOH group, or a protected group thereof (an $OR^X$ group, a $COOR^X$ group ($R^X$ is any substituent such as an alkyl group). As the linear saturated polyester, for example, those described in JP-A-2009-155479 or JP-A-2010-235824 can be suitably used, and the contents thereof are incorporated in the present specification.

Specific examples of the linear saturated polyester include polyethylene terephthalate (PET), polyethylene isophthalate, polybutylene terephthalate, poly(1,4-cyclohexylenedimethylene terephthalate), and polyethylene-2,6-naphthalate, and among these, polyethylene terephthalate or polyethylene-2,6-naphthalate is particularly preferable, and polyethylene terephthalate is more particularly preferable from the viewpoint of the balance between the dynamic strength and the cost. Moreover, whereas a film of polyethylene-2,6-naphthalate or polybutylene terephthalate is produced in a melt state by heating to 230° C. or higher during the film production, a film of PET is produced in a melt state by heating to 270° C. or higher, and thus, a ketene imine compound or a ketene compound is further easily generated, and in the polyester film of the present invention, it is possible to reduce the volatilization amount of the ketene imine compound or the ketene compound even in a case where the polyester is PET.

The polyester may be a homopolymer or a copolymer. Furthermore, it may be a blend of the polyester with a small amount of any other type of resin, for example, polyimide, or the like. In addition, it is also possible to use a crystalline polyester which can form anisotropy during film formation in a melt state as the polyester.

For the molecular weight of the polyester, the weight average molecular weight (Mw) is preferably 5000 to 100000, more preferably 8000 to 80000, and particularly preferably 12000 to 60000, from the viewpoint of heat resistance and viscosity. As the weight average molecular weight of the polyester, a value in terms of polymethyl methacrylate (PMMA), measured by gel permeation chromatography (GPC) using hexafluoroisopropanol as a solvent, can be used.

In the present invention, the ketene imine compound is preferably contained in 0.1% by mass to 2.0% by mass, more preferably contained in 0.15% by mass to 0.95% by mass, and still more preferably contained in 0.2% by mass to 0.9% by mass, with respect to the polyester included in the polyester resin composition. When the content of the ketene imine compound is within the above-described range, it is possible to improve hydrolysis resistance and film thickness uniformity of the polyester film of the present invention. Moreover, when the content ratio of the ketene imine compound is greater than the above-described upper limit value, the polyester film tends to be yellowed, and when the content ratio of the ketene imine compound is less than the above-described lower limit value, sufficient hydrolysis resistance tends not to be obtained, and thus, this is not preferable.

The polyester resin composition of the present invention does not refuse to include a compound other than the ketene imine compound of the present invention as long as it is not contrary to the spirit of the present invention. For example, the polyester resin composition of the present invention can be used in combination with a carbodiimide compound, an epoxy compound, or an oxazoline compound. The ketene imine compound of the present invention is preferably 70% by weight or greater, more preferably 80% by weight or greater, and particularly preferably 90% by weight or greater, with respect to an organic compound other than the polyester included in the polyester film of the present invention.

Furthermore, the polyester resin composition of the present invention preferably contains a pigment. Examples of the pigment include inorganic pigments such as titanium oxide, barium sulfate, silicon oxide, aluminum oxide, magnesium oxide, calcium carbonate, kaolin, talc, ultramarine blue, Prussian blue, carbon black, and the like; and organic pigments such as phthalocyanine blue, phthalocyanine green, and the like. Among these, a white pigment such as titanium oxide, barium sulfate, or calcium carbonate is preferably used, and titanium oxide is particularly preferably used.

These pigments scatter light such as sunlight incident, and conceal (reduce) the specific yellow which the ketene imine compound has. Among these, titanium oxide can more effectively scatter light, and has a high concealing ratio, and thus, titanium oxide is preferably used.

In addition, in the case of using the polyester film of the present invention in a back sheet for a solar cell module, a white pigment such as titanium oxide, barium sulfate, or calcium carbonate is preferably used from the viewpoint of constituting a colored layer as a reflective layer which reflects sunlight incident.

Furthermore, the pigment also suppresses volatilization of the ketene compound produced by the reaction of the ketene imine compound with a terminal carboxyl group of polyester. As this cause, it is considered that, by adsorption of the ketene compound on the particle surfaces of the pigment, the ketene compound is not volatilized outside the polyester film. Therefore, as the pigment, a pigment having favorable adsorption properties to the ketene compound is particularly preferably used.

In this manner, when volatilization of the ketene compound is suppressed, it is possible to suppress generation of gas including the ketene compound in the production step, and it is possible to improve the working environment in the production step.

The average particle diameter of the pigment is preferably 0.03 μm to 0.8 μm, and more preferably 0.15 μm to 0.5 μm in the volume average particle diameter. When the average particle diameter is within the above-described range, it is possible to increase light reflection efficiency. Moreover, the average particle diameter is a value which is measured by using a laser analysis/scattering type particle size distribution measuring device LA950 (manufactured by HORIBA, Ltd.).

The pigment is preferably added so as to be 1% by mass to 10% by mass, more preferably added so as to be 2% by mass to 9% by mass, and still more preferably added so as to be 3% by mass to 8% by mass, with respect to the total amount of polyester. Moreover, the pigment is preferably contained so as to be within the above-described range with respect to the polyester in the formed polyester film.

The terminal carboxyl group content (acid value of polyester, hereinafter, also referred to as AV) in the polyester is preferably 25 eq/ton or less, more preferably 20 eq/ton or less, still more preferably 16 eq/ton or less, and particularly preferably 15 eq/ton or less, with respect to the polyester. When the carboxyl group content is 25 eq/ton or less, the hydrolysis resistance and the heat resistance of a polyester film are maintained by combining with the ketene imine compound, and thus, reduction of strength at a time of wet heat aging can be suppressed low. The lower limit of the terminal carboxyl group content is desirably 10 eq/ton or greater from the viewpoint of keeping the adhesiveness (adhesive properties) among layers (for example, a white layer) formed when the polyester film of the present invention is used as the back sheet for a solar cell module. The terminal carboxyl group content in the polyester can be adjusted by the type of a polymerization catalyst, the polymerization time, or the film formation conditions (the film formation temperature and time). The carboxyl group content can be measured by a titration method according to the method described in H. A. Pohl, Anal. Chem. 26 (1954) 2145. Specifically, a polyester is dissolved in benzyl alcohol at 205° C. and a phenol red indicator is added. Then, titration is performed with a water/methanol/benzyl alcohol solution of sodium hydroxide, and from the titration amount, the acid value (eq/ton) can be calculated.

The terminal hydroxyl group content in the polyester is preferably 120 eq/ton or less, and more preferably 90 eq/ton or less, with respect to the polyester. When the hydroxyl group content is 120 eq/ton or less, the reaction between carbodiimide having a bulky functional group at a specific position described later and the hydroxyl group is suppressed, and thus, the reaction with a carboxyl group is preferentially undergone, which can further reduce the acid value. The lower limit of the hydroxyl group content is desirably 20 eq/ton or greater from the viewpoint of adhesiveness with an upper layer. The hydroxyl group content in the polyester can be adjusted by the type of a polymerization catalyst, the polymerization time, or the film formation conditions (the film formation temperature and time). As the terminal hydroxyl group content, a value measured by $^1$H-NMR using a deuterated hexafluoroisopropanol solvent can be used.

In addition, the intrinsic viscosity (IV) of the polyester film of the present invention is preferably 0.70 dl/g to 0.94 dl/g, more preferably 0.71 dl/g to 0.84 dl/g, and particularly preferably 0.72 dl/g to 0.84 dl/g. The intrinsic viscosity of the polyester film is preferably the lower limit value described above or less from the viewpoint of improving film formation properties and the film thickness uniformity.

For the intrinsic viscosity (IV) of polyester, in a case where polyester used during the film production is 2 or more types (for example, the case of using the retrieved polyester of JP-A-2011-256337 or the like), the intrinsic viscosity of polyester obtained by mixing all polyester preferably satisfies the above range.

For the intrinsic viscosity (IV) of polyester, polyester is dissolved in ortho-chlorophenol, and from the solution viscosity measured at 25° C., the intrinsic viscosity is obtained by the following equation.

$$\eta_{sp}/C=[\eta]+K[\eta]^2 \cdot C$$

Here, $\eta_{sp}$ is (solution viscosity/solvent viscosity)−1, C is the dissolved polymer weight per 100 mL of solvent (1 g/100 mL in this measurement), K is Huggins constant (0.343), and the solution viscosity and the solvent viscosity are measured using an Ostwald viscometer.

The polyester can be synthesized according to a known method. For example, polyester can be synthesized according to a known polycondensation method, a ring-opening polymerization method, or the like, which can be applied to any one of the reactions by transesterification reaction and direct polymerization.

In a case where the polyester used in the present invention is a polymer or copolymer, obtained by the condensation reaction of an aromatic dibasic acid or an derivative for forming an ester thereof with a diol or an derivative for forming an ester thereof as a main components, the polyester can be produced by subjecting an aromatic dibasic acid or a derivative for forming an ester thereof, and a diol or a derivative for forming an ester thereof to esterification reaction or transesterification reaction, and then to polycondensation reaction. In addition, by selecting the raw material or the reaction condition, the acid value or the intrinsic viscosity of the polyester can be controlled. Moreover, in order to perform the esterification or transesterification reaction and the polycondensation reaction effectively, it is preferable to add a polymerization catalyst during these reactions.

As the polymerization catalyst in the polymerization of the polyester, an Al-based, Sb-based, Ge-based, or Ti-based compound is preferably used from the viewpoint of inhibiting the carboxyl group content to a predetermined range or less, and among these, a Ti-based compound is particularly preferable. In the case of using a Ti-based compound, the Ti-based compound is used as the catalyst in the range of the amount of 1 ppm to 30 ppm, and more preferably 3 ppm to 15 ppm to perform polymerization. When the proportion of the Ti-based compound is within the range, it is possible to adjust the terminal carboxyl groups to fall within the range as described below, and it is also possible to keep the hydrolysis resistance of the polymer substrate low.

In the synthesis of the polyester using a Ti-based compound, for example, the methods described in JP-B-8-301198, Japanese Patent Nos. 2543624, 3335683, 3717380, 3897756, 3962226, 3979866, 3996871, 4000867, 4053837, 4127119, 4134710, 4159154, 4269704, 4313538, or the like can be applied, and the contents thereof are incorporated in the present specification.

Preferably, the polyester is one subjected to solid-phase polymerization after polymerization. Thus, it is possible to achieve a preferable acid value. The solid-phase polymerization may be in a continuous method (where the resin is filled in a tower, slowly circulated therein with heating for a predetermined period of time, and then discharged) or in a batch method (where the resin is put into a container and heated therein for a predetermined period of time). Specifically, the methods described in Japanese Patent Nos. 2621563, 3121876, 3136774, 3603585, 3616522, 3617340, 3680523, 3717392, 4167159, or the like can be applied to the solid-phase polymerization, and the contents thereof are incorporated in the present specification.

The temperature of the solid-phase polymerization is preferably 170° C. to 240° C., more preferably 180° C. to 230° C., and still more preferably 190° C. to 220° C. In addition, the time of the solid-phase polymerization is preferably 5 hours to 100 hours, more preferably 10 hours to 75 hours, and still more preferably 15 hours to 50 hours. The solid-phase polymerization is preferably performed in vacuum or in a nitrogen atmosphere.

(Polyester Film)

The present invention relates to a polyester film formed of the polyester resin composition described above.

The thickness of the polyester film of the present invention varies according to the uses, but in a case where the polyester film is used as a member of a back sheet for a solar cell module, the thickness is preferably 25 μm to 300 μm, and more preferably 120 μm to 300 μm. When the thickness is 25 μm or greater, a sufficient dynamic strength is obtained, and when the thickness is 300 μm or less, advantage in terms of cost is obtained.

The polyester film of the present invention is preferably stretched, more preferably biaxially stretched, and particularly preferably biaxially stretched in plane compared to stretching of a tubular shape, and more particularly preferably sequentially biaxially stretched. The degree of MD (Machine Direction: length direction) orientation and the degree of TD (Transverse Direction: width direction) orientation of the polyester film of the present invention are each preferably 0.14 or greater, more preferably 0.155 or greater, and particularly preferably 0.16 or greater. When each degree of orientation is 0.14 or greater, the restriction of the non-crystalline chain is improved (the mobility is lowered), and the hydrolysis resistance is improved. The degree of MD orientation and the degree of TD orientation can be calculated from the degree of MD orientation: $\Delta n(x-z)$, the degree of TD orientation; $\Delta n(y-z)$, by measuring the refractive indices in the x, y, and z directions of the biaxially oriented film at an atmosphere at 25° C., using an Abbe refractometer, a monochromatic light sodium D-line as the light source, and methylene iodine as a mount solution.

In addition, the intrinsic viscosity (IV) of the polyester film of the present invention is preferably 0.70 dl/g to 0.94 dl/g, more preferably 0.71 dl/g to 0.84 dl/g, and particularly preferably 0.72 dl/g to 0.84 dl/g. The intrinsic viscosity of the polyester film is preferably the lower limit value described above or less from the viewpoint of improving film formation properties and the film thickness uniformity.

Moreover, within a range not interfering with the effects of the present invention, various additives, for example, a compatibilizer, a plasticizer, a weathering agent, an antioxidant, a thermal stabilizer, a lubricant, an antistatic agent, a brightener, a colorant, a conductive agent, an ultraviolet absorber, a flame retardant, a flame retardant auxiliary agent, a pigment, a dye, or the like may be added to the polyester film of the present invention.

(Production Method of Polyester Film)

(Film Forming Step)

In the film forming step, the melt obtained by meting the polyester and the ketene imine compound included in the resin composition for forming the polyester film of the present invention is passed through a gear pump or a filter, then extruded to a cooling roll through a die, and cooled and solidified, whereby a (unstretched) film can be formed. Moreover, the extruded melt can be adhered to the cooling roll using an electrostatic application method. At this time, the surface temperature of the cooling roll can be usually set to 10° C. to 40° C.

(Stretching Step)

The (unstretched) film formed by the film forming step can be realized by performing a stretching treatment in the stretching step. In the stretching step, a film cooled and solidified (unstretched) by the cooling roll is preferably stretched in one or two directions, and more preferably stretched in two directions. The stretching in two directions (biaxial stretching) is preferably stretching in the length direction (MD: Machine Direction) (hereinafter, also referred to as "longitudinal stretching") and in the width direction (TD: Transverse Direction) (hereinafter, also referred to as a "transverse stretching"). The longitudinal stretching and the transverse stretching may be performed once, respectively, or may be performed plural times, and the longitudinal stretching and the transverse stretching may be performed at the same time.

The stretching treatment is performed, preferably at the glass temperature (Tg)° C. of the film to (Tg+60)° C., more preferably Tg+3° C. to Tg+40° C., and still more preferably at Tg+5° C. to Tg+30° C.

The preferable stretching ratio is 280% to 500%, more preferably 300% to 480%, and still more preferably 320% to 460% in at least one direction. In the case of biaxial stretching, the stretching may be performed equivalently in the longitudinal and the transverse directions, but it is more preferable that the stretching ratio in one direction is greater than that in the other direction, thereby performing inequivalent stretching. Any one of the longitudinal direction (MD) and the transverse direction (TD) may be greater than the other. The stretching ratio as mentioned herein is determined using the following equation.

Stretching ratio (%)=100×(Length after stretching)/ (Length before stretching)

The biaxial stretching treatment is a stretching, for example, at the glass transition temperature $(Tg_1)$° C. of a film to $(Tg_1+60)$° C. in the length direction once or two or more times, in which the total ratio is 3- to 6-times and the ratio in the width ration at $(Tg_1)$° C. to (Tg+60)° C. is 3- to 5-times.

The biaxial stretching treatment can be carried out by stretching in the length direction, using two or more nip rolls that have a higher peripheral speed at an outlet (longitudinal stretching), and can also carried out by gripping both ends of the film with chucks and extending them in the perpendicular direction (the direction perpendicular to the length direction) (transverse stretching).

In the stretching step, before the stretching treatment or after the stretching treatment, and preferably after stretching treatment, the film can be subjected to a heat treatment. By performing the heat treatment, fine crystals can be produced, thereby improving the dynamic characteristics or durability. The film can also be subjected to a heat treatment at about 180° C. to 210° C. (more preferably at 185° C. to 220° C.) for 1 second to 60 seconds (more preferably for 2 seconds to 30 seconds).

In the stretching step, the thermal relaxation treatment can be performed after the heat treatment. The thermal relaxation treatment is a treatment for shrinking the film by applying heat to the film for stress relaxation. The thermal relaxation treatment is preferably performed in both directions of MD and TD of the film. For the conditions in the thermal relaxation treatment, the treatment is performed preferably at a temperature lower than the heat treatment temperature, and more preferably at 130° C. to 220° C. In addition, for the thermal relaxation treatment, the thermal shrinkage (150° C.) of the film in both of the MD and the TD is preferably 1% to 12%, and more preferably 1% to 10%. However, the thermal shrinkage (150° C.) is determined as follows. The thermal shrinkage can be determined from the following equation, by cutting out a sample having a width of 50 mm at 350 mm in the measurement direction, attaching a target point at an interval of 300 mm near the both ends in the length direction of the sample, fixing one end in an oven adjusted to a temperature of 150° C., leaving the other end to be free for 30 minutes, then measuring the distance between the target points at room temperature, taking this length as L (mm), and using this measured values.

$$150° C.\ \text{thermal shrinkage}\ (\%)=100\times(300-L)/300$$

In addition, a case where the thermal shrinkage is positive denotes shrinkage, and a case where the thermal shrinkage is negative denotes stretching.

As described above, according to the method described above, a film having excellent hydrolysis resistance can be fabricated. The polyester film of the present invention can be suitably used not only as a protective sheet (back sheet for a solar cell module) for a solar cell module as described below, but also in other applications.

In addition, the film of the present invention can also be used as a laminate including a coating layer containing at least one functional group selected from COOH, OH, $SO_3H$, $NH_2$, and a salt thereof thereon.

[Back Sheet for Solar Cell Module]

The polyester film of the present invention can also be used as a laminate film provided with a coating layer such as a readily adhesive layer thereon. The polyester film or the laminate film of the present invention is widely used for various purposes, and is suitably used as a back sheet for a solar cell module (protective sheet for a solar cell module). The polyester film of the present invention has excellent adhesiveness and wet heat resistance, and thus, in the case of using the polyester film of the present invention in a back sheet for a solar cell module, a solar cell module can be protected over a long period of time, and the power generation efficiency of the solar cell module is not deteriorated. In addition, since yellowing of the polyester film of the present invention is suppressed, the design characteristics of the solar cell module are also not deteriorated.

By laminating the following functional layers on the polyester film of the present invention, it is possible to form a back sheet for a solar cell module. When laminating functional layers, a readily adhesive layer is preferably provided therebetween. Moreover, before laminating functional layers, the surface of the polyester film is preferably subjected to a surface treatment, and, for example, a flame treatment, a corona treatment, a plasma treatment, or an ultraviolet treatment can be performed.

<Reflective Layer (Colored Layer)>

A light reflective layer is preferably provided to the inner side surface (side to be adhered to a sealing material) of the back sheet of the present invention. By providing a reflective layer, it is possible to return the light to the solar cell by reflecting the light which passes through the solar cell and reaches the back sheet, in sunlight which is incident to the solar cell module. Thus, it is possible to improve the power generation efficiency.

Furthermore, the reflective layer preferably has an adhesive strength of 10 N/cm or greater, and more preferably 20 N/cm or greater, with respect to the sealing material.

(Binder)

First, the binder of the reflective layer will be described. As the binder of the reflective layer of the present invention, an acryl-based polymer, a polyester-based polymer, a polyurethane-based polymer, a polyolefin-based polymer, or the like can be used, and among these, the polyolefin-based polymer is preferable.

The reflective layer of the present invention preferably contains a crosslinking agent such as an epoxy-based crosslinking agent, an isocyanate-based crosslinking agent, an oxazoline-based crosslinking agent, or a carbodiimide-based crosslinking agent in order to further improve adhesive properties to the sealing material.

Among these crosslinking agents, the carbodiimide-based crosslinking agent and the oxazoline-based crosslinking agent are particularly preferable from the viewpoint of ensuring adhesive properties after wet heat aging. The carbodiimide-based crosslinking agent used in the present invention is a compound having one or more carbodiimide groups in the molecule.

A white pigment is preferably added to the reflective layer of the present invention for the purpose of increasing reflectance.

Preferable examples of the white pigment can include titanium oxide, barium sulfate, silicon oxide, aluminum oxide, magnesium oxide, calcium carbonate, kaolin, and talc. Among these, titanium oxide is particularly preferable from the viewpoint of whiteness, reflectance, and durability. Although there are three types of crystal systems of rutile, anatase, and brookite in the titanium oxide, titanium oxide having a rutile-type crystalline structure is preferable from high refractive index, high whiteness, and a low photocatalytic activity.

To the reflective layer of the present invention, as necessary, a known additive such as a surfactant or a preservative may be added.

Examples of the surfactant can include known surfactants such as an anionic surfactant and a nonionic surfactant. Examples of the anionic surfactant include sodium alkylsulfate and sodium alkylbenzene sulfonate, and examples of the nonionic surfactant include polyoxyethylene alkyl ether. In addition, a fluorine-based surfactant such as sodium perfluoroalkyl sulfate is also preferable.

The thickness of the reflective layer of the present invention is preferably in the range of 3 μm to 10 μm, and more preferably in the range of 4 μm to 8 μm.

When the thickness of the reflective layer is in the range of 3 μm to 10 μm, it is possible to achieve both reflectance and adhesive properties required.

A method of coating the reflective layer of the present invention is not particularly limited, but known coating methods such as a roll coating method, a bar coating method, a slide-die method, and a gravure coating method can be used.

The coating solvent is also not limited, organic solvent-based solvents such as methyl ethyl ketone, toluene, and xylene may be used, or water may be used as a solvent. However, in consideration of low environmental burden, coating using water as a solvent is particularly preferable. These coating solvents may be used alone or may be used in combination. In particular, in the case of water-based coating solvent, the solvent may be used as a mixed solvent obtained by mixing a small amount of water-miscible organic solvent with water.

Drying of the reflective layer is also not particularly limited, but drying is preferably performed at a temperature of about 120° C. to 200° C. for about 1 minute to 10 minutes from the viewpoint of shortening the drying time. In a case where the drying temperature is lower than 120° C., dying time becomes longer, and thus, this is disadvantageous in production thereof. In contrast, in a case where the drying temperature is higher than 200° C., the flatness of the obtained back sheet is impaired in many cases.

<Overcoat Layer>

For the purposes of improving adhesive properties to the sealing material, an overcoat layer may be provided on the reflective layer in the back layer of the present invention.

As the binder of the overcoat layer, those described in <Reflective Layer> can be preferably used.

As the type of the crosslinking agent of the overcoat layer, those described in <Reflective Layer> can be preferably used.

The content of the crosslinking agent of the overcoat layer is preferably 5% by mass to 40% by mass, and more preferably 10% by mass to 30% by mass, with respect to the binder constituting the overcoat layer. When the content of the crosslinking agent is 5% by mass or greater, it is possible to obtain a sufficient crosslinking effect while keeping the strength of the polymer layer and the adhesive properties, and when the content of the crosslinking agent is 40% by mass or less, the pot life of the coating liquid can be maintained longer.

As the types of and the amounts added of other additives in the overcoat layer, those described in <Reflective Layer> can be preferably used.

The film thickness of the overcoat layer is preferably in the range of 0.1 μm to 1.0 μm, and more preferably in the range of 0.2 μm to 0.8 μm. When the thickness of the overcoat layer is in the range of 0.1 μm to 1.0 μm, it is possible to obtain high adhesive properties to the sealing material.

As the coating method, the coating solvent, and the drying method of the overcoat layer, those or the method described in <Reflective Layer> can be preferably used.

<Rear Surface Layer>

The back sheet of the present invention is provided with a rear surface layer for protecting a support on the outer surface (the surface of the opposite side of a solar cell).

First, the binder of the rear surface layer will be described. As the binder of the rear surface layer, the silicone-based complex polymers described below are preferably used from the viewpoint of durability and adhesive properties to the support. The silicone-based complex polymer (hereinafter, sometimes referred to as "complex polymer") of the present invention is a polymer including a —$(Si(R^1)(R^2)$—$O)_n$— moiety and a polymer structure moiety which is copolymerized with the moiety in the molecule.

By using the silicone-based complex polymer as the binder of the rear surface layer, it is possible to make the adhesive properties between the rear surface layer and the support particularly favorable, and it is possible to keep reduction of the adhesive properties low over a long period of time.

The silicone-based complex polymer preferably takes the form of a water-based polymer dispersion (so-called latex). The preferable particle diameter of latex of the silicone-based complex polymer is about 50 nm to 500 nm, and the preferable concentration is about 15% by mass to 50% by mass.

In a case where the water-based polymer has the form of latex, the silicone-based complex polymer of the present invention preferably has a functional group with water affinity such as a carboxyl group, a sulfonic acid group, a hydroxyl group, or an amide group. In a case where the silicone-based complex polymer of the present invention has a carboxyl group, the carboxyl group may be neutralized with sodium, ammonium, or amine.

In addition, in the case of being used in the form of latex, an emulsion stabilizer such as a surfactant (example: anionic or nonionic surfactant) or a polymer (example: polyvinyl alcohol) may be contained in order to improve the stability. Furthermore, as necessary, compounds known as an additive in latex such as a pH adjusting agent (example: ammonia, triethylamine, or sodium hydrogen carbonate), a preservative (example: 1,3,5-hexahydro-(2-hydroxyethyl)-s-triazine, or 2-(4-thiazolyl)benzimidazole), a thickening agent (example: sodium polyacrylate, or methyl cellulose), and a film-forming assistant (example: butyl carbitol acetate) may be added.

A crosslinking agent is preferably added to the rear surface layer of the present invention in order to improve the adhesive properties to the support. As the type of the crosslinking agent, those described in <Reflective Layer> can be used.

The content of the crosslinking agent is preferably 5% by mass to 40% by mass, and more preferably 10% by mass to 30% by mass, with respect to the binder constituting the rear surface layer. When the content of the crosslinking agent is 5% by mass or greater, it is possible to obtain a sufficient crosslinking effect while keeping the adhesive properties to the support, and when the content of the crosslinking agent is 40% by mass or less, the pot life of the coating liquid can be maintained longer.

An ultraviolet absorber is preferably added to the rear surface layer of the present invention.

In the case of an organic-based ultraviolet absorber, examples of the ultraviolet absorber include ultraviolet absorbers such as a salicylic acid-based absorber, a benzophenone-based absorber, a benzotriazole-based absorber, and a cyanoacrylate-based absorber and ultraviolet stabilizers such as a hindered amine-based stabilizer.

In addition, examples of an inorganic-based ultraviolet absorber include metal oxides such as titanium oxide, zinc oxide, and cerium oxide, and carbon-based components such as carbon, fullerene, a carbon fiber, and a carbon nanotube. Among these, titanium oxide is particularly preferable from the viewpoint of cost and durability.

Although the amount of ultraviolet absorber added to the rear surface layer varies depending on the type of the ultraviolet absorber, the amount is preferably in the range of 0.2 g/m$^2$ to 5 g/m$^2$, and more preferably in the range of 0.3 g/m$^2$ to 3 g/m$^2$.

A white pigment may be added to the rear surface layer for the purpose of compensating for the reflectance of the reflective layer. As the type of the white pigment, the white pigments described in <Reflective Layer> can be preferably used.

The amount of the white pigment added to the rear surface layer is preferably in the range of 0.3 g/m$^2$ to 10 g/m$^2$, and more preferably in the range of 4 g/m$^2$ to 9 g/m$^2$. When the amount added is 0.3 g/m$^2$ to 10 g/m$^2$, it is possible to achieve both excellent adhesive properties and reflectance improvement. Moreover, in the case of using titanium oxide as the white pigment, it is possible to serve as both a pigment and an ultraviolet absorber. As the types of and the amounts added of other additives in the rear surface layer, those described in <Reflective Layer> can be preferably used.

The thickness of the rear surface layer is preferably in the range of 3 μm to 12 μm, and more preferably in the range of 4 μm to 8 μm.

When the thickness of the rear surface layer is in the range of 3 μm to 12 μm, it is possible to achieve both durability and adhesive properties required.

As the coating method, the coating solvent, and the drying method of the rear surface layer, those or the method described in <Reflective Layer> can be preferably used.

<Rear Surface Protective Layer>

For the purposes of further improving durability, a rear surface protective layer may be provided on the rear surface layer in the back sheet of the present invention.

The binder of the rear surface protective layer of the present invention is preferably a fluorine-based polymer from the viewpoint of durability.

The fluorine-based polymer capable of being preferably used in the present invention is a polymer including a fluorine-containing monomer in the main chain or the side chain. Although the fluorine-containing monomer may be included in any one of the main chain or the side chain, the fluorine-containing monomer is preferably included in the main chain from the viewpoint of durability.

In the case of using the fluorine-based polymer of the present invention in the form of latex, the particle diameter is preferably about 50 nm to 500 nm, and the solid content concentration is preferably about 15% by mass to 50% by mass.

In a case where the water-based polymer has the form of latex, the fluorine-based polymer of the present invention preferably has a functional group with water affinity such as a carboxyl group, a sulfonic acid group, a hydroxyl group, or an amide group.

A crosslinking agent is preferably added to the rear surface protective layer of the present invention in order to improve the adhesive properties to the support. As the type of the crosslinking agent, those described in <Reflective Layer> can be used.

To the rear surface protective layer of the present invention, as necessary, a slipping agent may be added.

Examples of the slipping agent include a synthetic wax-based compound, a natural wax-based compound, a surfactant-based compound, an inorganic compound, and an organic resin-based compound. Among these, from the viewpoint of the surface strength of the polymer layer, a compound selected from a synthetic wax-based compound, a natural wax-based compound, and a surfactant-based compound is preferable.

To the rear surface protective layer of the present invention, as necessary, colloidal silica may be added.

The colloidal silica which can be used in the present invention is colloidal silica in which fine particles having silicon oxide as a main component are present in a fine particle state in water, monovalent alcohols, diols, or a mixture thereof as a dispersion medium.

As the types of and the amounts added of other additives in the rear surface protective layer, those described in <Reflective Layer> can be preferably used.

The thickness of the rear surface protective layer is preferably in the range of 0.5 μm to 6 μm, and more preferably in the range of 1 μm to 5 μm. When the thickness of the rear surface protective layer is less than 0.5 μm, durability is insufficient in some cases, and when the thickness is greater than 6 μm, it is disadvantageous in terms of cost.

As the coating method, the coating solvent, and the drying method of the rear surface protective layer, those or the method described in <Reflective Layer> can be preferably used.

[Solar Cell Module]

The solar cell module of the present invention includes the polyester film of the present invention or the back sheet for a solar cell module of the present invention.

The solar cell module of the present invention is constituted such that a solar cell element that converts the light energy of sunlight to electrical energy is arranged between a transparent substrate, on which sunlight is incident, and the polyester film (back sheet for a solar cell) of the present invention. The space between the substrate and the polyester film can be constituted to be sealed with a resin (a so-called sealing agent) such as an ethylene-vinyl acetate copolymer.

The details of the solar cell module, the solar cell, and the members other than the back sheet are described in, for example, "Constituent Materials for Sunlight Power Generation System" (edited by Eiichi Sugimoto, Kogyo Chosakai Publishing Co., Ltd. published in 2008).

The transparent substrate may have light transmitting properties by which sunlight can be transmitted, and can be suitably selected from base materials that transmit light. From the viewpoint of power generation efficiency, a base material having higher light transmittance is preferable, and as such a substrate, for example, a glass substrate, a substrate of a transparent resin such as an acrylic resin can be suitably used.

As the solar cell element, various known solar cell elements such as silicon-based elements such as single crystal silicon, polycrystalline silicon, and amorphous silicon; and Group III-V or Group II-VI compound semiconductor-based elements such as copper-indium-gallium-selenium, copper-indium-selenium, cadmium-tellurium, and gallium-arsenic can be applied.

EXAMPLES

Hereinafter, characteristics of the present invention will be more specifically described with reference to Examples and Comparative Examples. The materials, amounts used, proportions, treatment contents, treatment procedures, and the like indicated in the Examples below may be changed as appropriate without departing from the spirit of the present invention. Therefore, the scope of the present invention is not to be interpreted as limiting to the specific examples shown below.

The ketene imine compound represented by Formula (1) of the present invention, having the following structure was used as a terminal blocking agent in each Example. Moreover, "DMSO" described below is the abbreviation of dimethylsulfoxide.

Exemplary Compound (1)

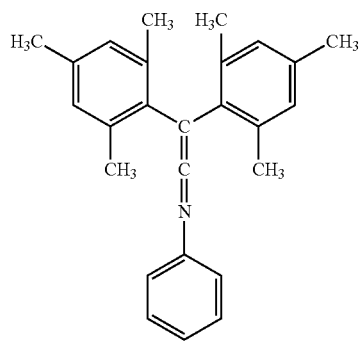

Exemplary Compound (5)

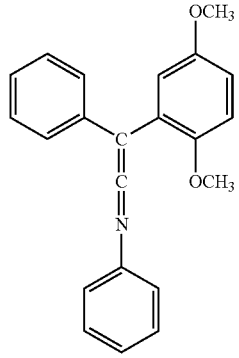

Exemplary Compound (18)

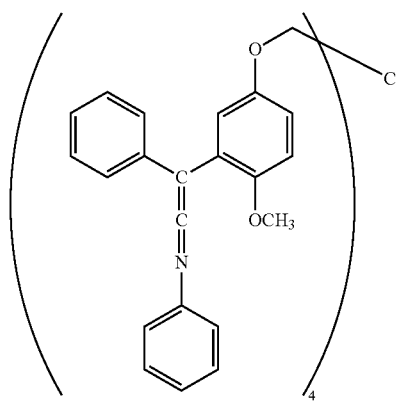

Exemplary Compound (21)

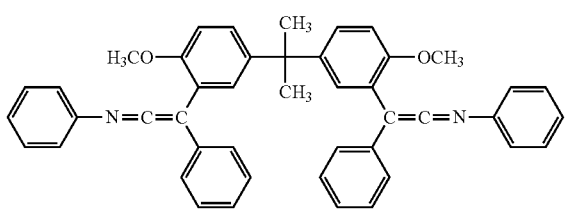

Exemplary Compound (22)

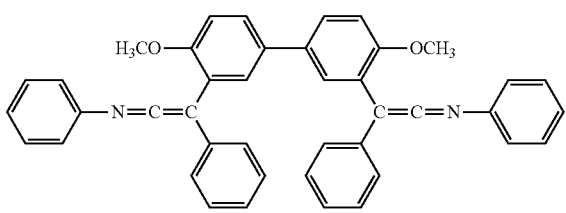

Exemplary Compound (41)

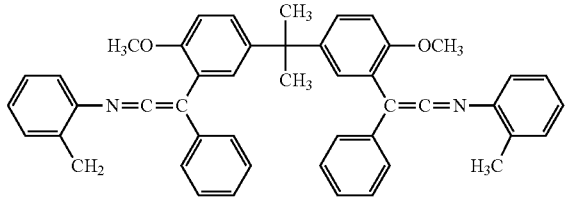

Exemplary Compound (45)

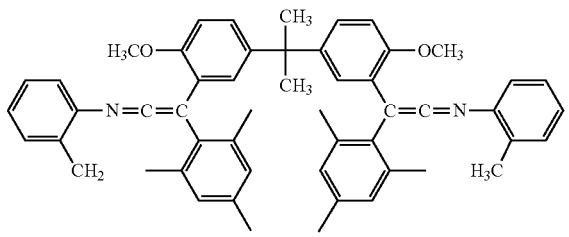

Exemplary Compound (61)

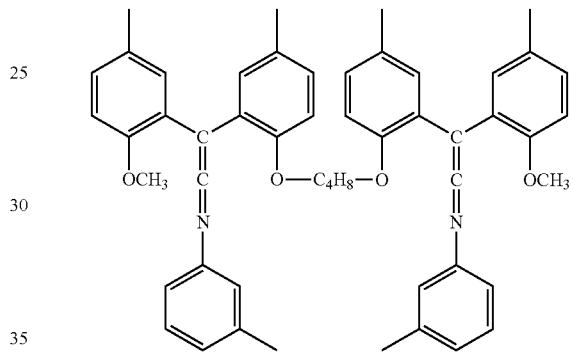

Synthesis Example 1

Synthesis of Exemplary Compound 1

50 mL of methanesulfonic acid and 50 mL acetic acid were added to a mixture of 2.4 g (20 mmol) of mesitylene and 0.8 g (9 mmol) of glyoxylic acid monohydrate, followed by stirring at 80° C. for 4 hours. After this was extracted with ethyl acetate, the resultant product was washed with distilled water and concentrated, whereby a white solid was obtained. After this was dissolved in 100 mL of dichloromethane, 1.18 g (10 mmol) of thionyl chloride was added dropwise thereto, and the resultant product was heated to reflux for 6 hours. The remaining thionyl chloride was distilled off under reduced pressure, and 1.9 g (20 mmol) of aniline was added thereto, followed by stirring at 70° C. for 2 hours. After this was extracted with ethyl acetate, the resultant product was washed with a 1 N aqueous hydrochloric acid solution, and the organic layer was concentrated under reduced pressure, whereby a white solid was obtained.

This was dissolved in 50 mL of chloroform, and 1.02 g (10 mmol) of triethylamine, 2.1 g (8 mmol) of triphenylphosphine, and 1.27 g (8 mmol) of carbon tetrachloride were added thereto, followed by reacting at 65° C. for 6 hours. After ethyl acetate was added to this, the filtrate was concentrated, and purified by column chromatography (hexane/ethyl acetate=10/1), whereby 1.2 g (3.3 mmol, yield of 33%, yellow solid) of Exemplary Compound 1 was obtained. $^1$H-NMR (DMSO-d6): 2.12 (s, 12H), 2.17 (s, 6H), 7.0-7.5 (m, 5H)

Synthesis Example 2

Synthesis of Exemplary Compound 5

300 mL of 73% sulfuric acid was added to a mixture of 138 g (1.25 mol) of hydroquinone and 76 g (0.50 mol) of mandelic acid, followed by heating and stirring at 100° C. for 30 minutes. The resultant product was poured into 2 L of ice water, and the produced pale pink solid was collected by filtration and washed with pure water. Furthermore, the resultant product was recrystallized from 500 mL of toluene, whereby 102 g (0.45 mmol, yield of 90%, pale pink solid) of Intermediate 5A was obtained. $^1$H-NMR (DMSO-d6): 5.28 (s, 1H), 6.54 (s, 1H), 6.74 (d, 1H), 7.10 (d, 1H), 7.31 (d, 2H), 7.3-7.5 (m, 3H)

30.7 g (0.33 mol) of aniline was added to 15.0 g (66.3 mmol) of Intermediate 5A, followed by heating and stirring at 125° C. for 2 hours. After the resultant product was cooled to room temperature, 200 mL of ethyl acetate was added thereto, and the produced white solid was collected by filtration, washed with ethyl acetate, and air-dried, whereby 21.0 g (66.1 mmol, yield of 99%, white solid) of Intermediate 5B was obtained. $^1$H-NMR (DMSO-d6): 5.34 (s, 1H), 6.45 (s, 1H), 6.62 (d, 2H), 7.01 (t, H), 7.2-7.4 (m, 7H), 7.64 (d, 2H), 8.60 (s, 1H), 8.94 (s, 1H), 10.30 (s, 1H)

7.5 g (23.5 mmol) of Intermediate 5B and 19.3 g (0.14 mol) of potassium carbonate were put into a 100 mL flask, and replacement by nitrogen gas was performed. In a nitrogen atmosphere, 30 mL of acetone and 19.8 g (0.14 mol) of iodomethane were added thereto, followed by stirring at room temperature for 6 hours. Then, after the resultant product was crystallized from 300 mL of pure water, the obtained product was collected by filtration, dried, and recrystallized from methanol, whereby 6.2 g (17.8 mmol, yield of 76%, white solid) of Intermediate 5C was obtained. $^1$H-NMR (DMSO-d6): 3.63 (s, 3H), 3.70 (s, 3H), 5.38 (s, 1H), 6.70 (s, 1H), 6.81 (d, 1H), 6.92 (d, 1H), 7.02 (t, 1H), 7.2-7.4 (m, 7H), 7.61 (d, 2H), 10.3 (s, 1H)

16.1 g (46.4 mmol) of Intermediate 5C was dissolved in 100 mL of chloroform, and 15.8 g (60.3 mmol) of triphenylphosphine, 9.4 g (92.8 mmol) of triethylamine, and 9.6 g (60.3 mmol) of carbon tetrachloride were added thereto, followed by heating and stirring at 65° C. for 8 hours. Then, the reaction liquid was cooled to room temperature, and crystallized from 400 mL of hexane. The filtrate was concentrated, and purified by column chromatography (hexane/ethyl acetate=3/1), whereby 10.2 g (yield of 67%, yellow solid) of Exemplary Compound 5 was obtained. $^1$H-NMR (DMSO-d6): 3.63 (s, 6H), 6.64 (s, 1H), 6.86 (d, 1H), 7.03 (d, 1H), 7.25 (t, 3H), 7.3-7.5 (m, 7H)

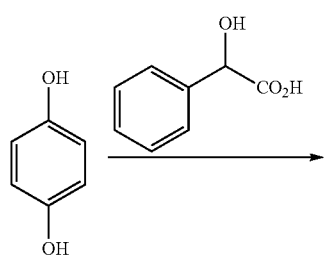

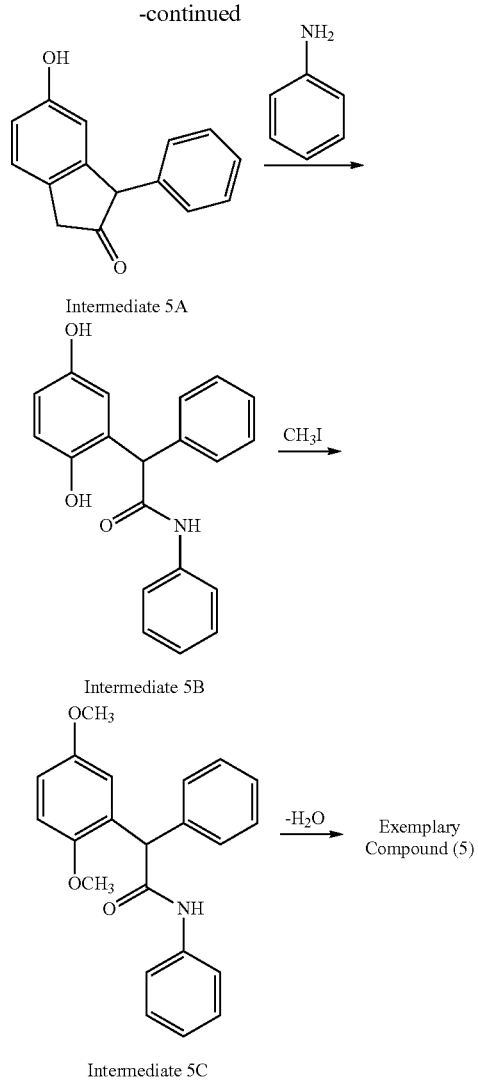

Synthesis Example 3

Synthesis of Exemplary Compound 18

Intermediate 5B (4.2 mmol) was dissolved in acetone, and potassium carbonate (4.2 mmol) and pentaerythritol tetrabromide (1.0 mmol) were added thereto, followed by heating and stirring at 60° C. for 2 hours. Then, the temperature was returned to room temperature, and potassium carbonate (8.4 mmol) and iodomethane (8.4 mmol) were added thereto, followed by stirring at room temperature for 4 hours. The white solid obtained by crystallizing this from pure water was purified by column chromatography (hexane/ethyl acetate=4/1), whereby Intermediate 18A was obtained. $^1$H-NMR (DMSO-d6): 3.65 (s, 12H), 4.30 (s, 8H), 5.40 (s, 4H), 6.75 (s, 4H), 6.78 (d, 4H), 6.90 (d, 4H), 7.06 (t, 4H), 7.2-7.4 (m, 28H), 7.65 (d, 8H), 10.1 (s, 4H)

2.3 g (1.6 mmol) of Intermediate 18A was dissolved in 30 mL of chloroform, and 2.6 g (9.9 mmol) of triphenylphosphine, 1.3 g (13.2 mmol) of triethylamine, and 1.0 g (6.6 mmol) of carbon tetrachloride were added thereto, followed by heating and stirring at 65° C. for 8 hours. Then, the reaction liquid was cooled to room temperature, and crystallized from 200 mL of hexane. The filtrate was concentrated, and purified by column chromatography (hexane/ethyl acetate=3/1), whereby 1.2 g (yellow solid, yield of 78%) of Exemplary Compound 18 was obtained. $^1$H-NMR (DMSO-d6): 3.63 (s, 12H), 4.32 (s, 8H), 6.64 (s, 4H), 6.86 (d, 4H), 7.03 (d, 4H), 7.25 (t, 12H), 7.3-7.5 (m, 28H)

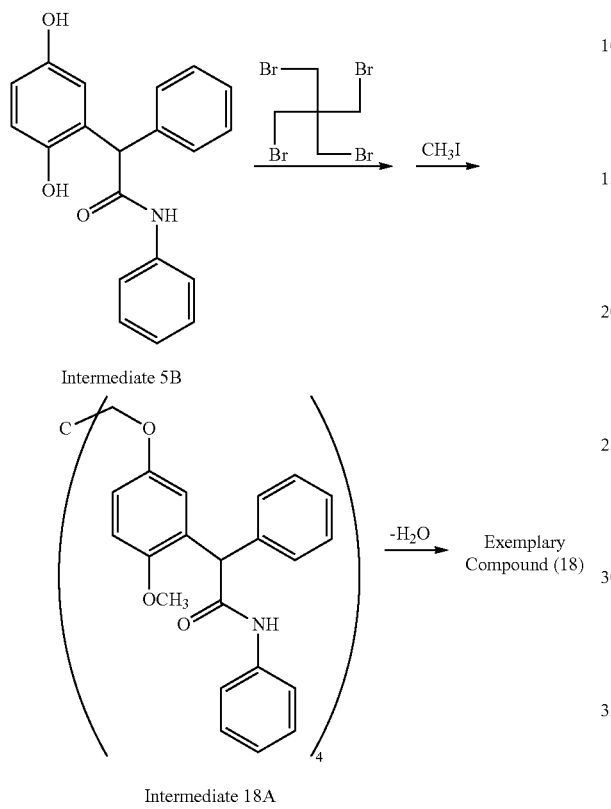

Synthesis Example 4

Synthesis of Exemplary Compound 21

40 g (0.175 mol) of bisphenol A and 64 g (0.21 mol) of mandelic acid were put into a 300 mL flask, then, the pressure was reduced at 220° C., and the mixture was heated and stirred for 6 hours while distilling off the water produced using a Dean-Stark trap. This was cooled to room temperature, dissolved in, and extracted with ethyl acetate, then, the resultant product was washed with distilled water and dried over magnesium sulfate, and the organic layer was concentrated, whereby 72 g (0.158 mmol, yield of 90%, orange solid) of Intermediate 21 was obtained. $^1$H-NMR (DMSO-d6): 1.54 (s, 6H), 5.30 (s, 2H), 7.01 (s, 2H), 7.12 (d, 4H), 7.18 (s, 4H), 7.32 (m, 6H)

13.6 g (29.5 mmol) of Intermediate 21A was dissolved in 27.9 g (0.3 mol) of aniline, followed by heating and stirring at 120° C. for 3 hours. The reaction liquid was diluted with methanol, and crystallized from 1 N aqueous hydrochloric acid, and the produced solid was collected by filtration, and air-dried, whereby 17.2 g (26.2 mmol, yield of 89%, pale yellow solid) of Intermediate 21B was obtained. $^1$H-NMR (DMSO-d6): 1.35 (s, 6H), 5.29 (s, 2H), 6.62 (d, 2H), 6.74 (d, 2H), 7.0-7.3 (m, 18H), 7.56 (m, 4H), 9.43 (s, 2H), 10.26 (s, 2H)

20.0 g (30.9 mmol) of Intermediate 21B was dissolved in acetone, and 16.6 g (0.12 mol) of potassium carbonate and 17.0 g (0.12 mol) of iodomethane were added thereto, followed by stirring at room temperature for 7 hours. After this was extracted with ethyl acetate, the resultant product was washed with distilled water, and the organic layer was dried, concentrated, and purified by column chromatography (hexane/ethyl acetate=3/1), whereby 7.6 g (11.3 mmol, yield of 37%, white solid) of Intermediate 21C was obtained. $^1$H-NMR (DMSO-d6): 1.37 (s, 6H), 3.68 (s, 6H), 5.31 (s, 2H), 6.79 (d, 2H), 6.9-7.2 (m, 20H), 7.53 (t, 4H), 10.2 (s, 2H)

7.2 g (10.7 mmol) of Intermediate 21C was dissolved in 50 mL of chloroform, and 7.3 g (27.9 mmol) of triphenylphosphine, 4.3 g (42.8 mmol) of triethylamine, and 4.4 g (27.9 mmol) of carbon tetrachloride were added thereto, followed by heating and stirring at 65° C. for 8 hours. Then, the reaction liquid was cooled to room temperature, and crystallized from 200 mL of hexane/ethyl acetate of 2/1. The filtrate was concentrated, and purified by column chromatography (hexane/ethyl acetate=5/2), whereby 5.1 g (7.9 mmol, yield of 74%, yellow solid) of Exemplary Compound 21 was obtained. $^1$H-NMR (DMSO-d6): 1.47 (s, 6H), 3.62 (s, 6H), 6.83 (s, 2H), 6.99 (dd, 6H), 7.13 (m, 4H), 7.22 (t, 4H), 7.31 (m, 6H), 7.42 (t, 4H)

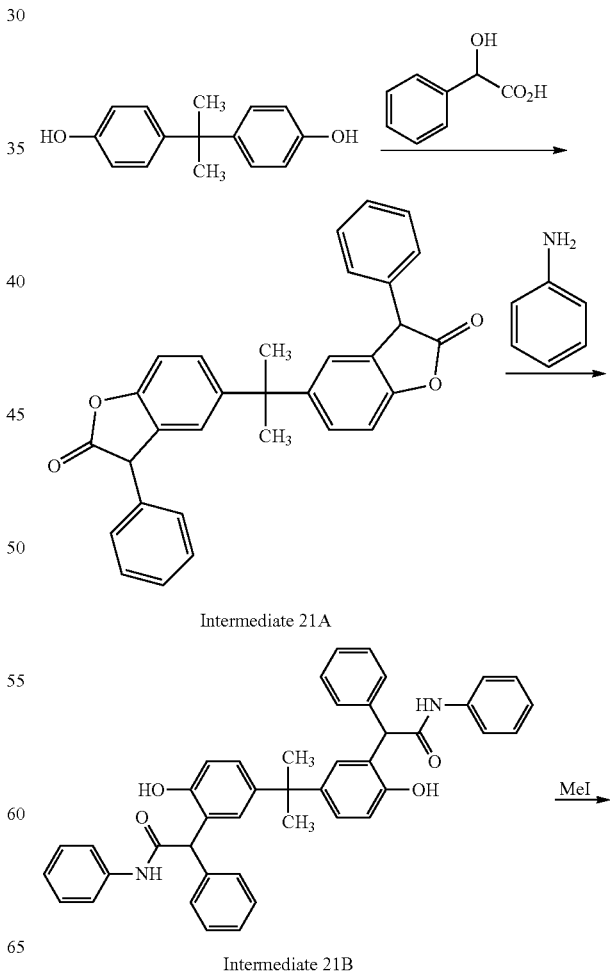

-continued

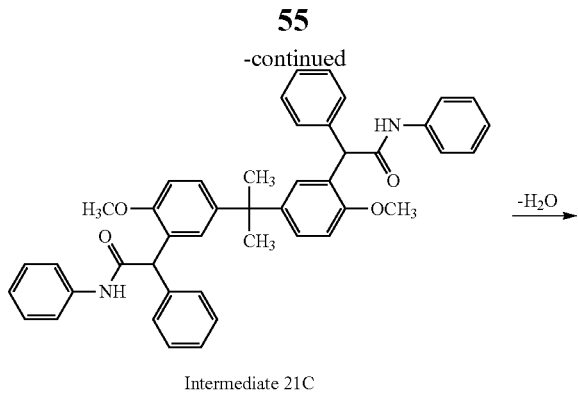

Intermediate 21C

Exemplary Compound (21)

Synthesis Example 5

Synthesis of Exemplary Compound 22

Exemplary Compound 22 was synthesized in the same manner as in Exemplary Compound 21 except that biphenol was used instead of bisphenol A. $^1$H-NMR (DMSO-d6): 3.72 (s, 6H), 7.1-7.5 (m, 26H)

Synthesis Example 6

Synthesis of Exemplary Compound 41

Exemplary Compound 41 was synthesized in the same manner as in Exemplary Compound 21 except that o-toluidine was used instead of aniline. $^1$H-NMR (DMSO-d6): 1.47 (s, 6H), 2.23 (s, 6H), 3.67 (s, 6H), 6.8-7.6 (m 24H)

Synthesis Example 7

Synthesis of Exemplary Compound 45

Exemplary Compound 45 was synthesized in the same manner as in Exemplary Compound 21 except that 2-hydroxy-2-(2,4,6-trimethylphenyl)-propionic acid was used instead of mandelic acid and o-toluidine was used instead of aniline. $^1$H-NMR (DMSO-d6): 1.31 (s, 6H), 2.09 (s, 6H), 2.12 (s, 12H), 2.17 (s, 6H), 3.44 (s, 6H), 6.7-7.2 (m, 18H)

Synthesis Example 8

Synthesis of Exemplary Compound 61

750 mL of acetic acid, 610 g (5.0 mol) of p-methylanisole, and 437 g (4.75 mol) of glyoxylic acid monohydrate were put into a 5 L three-necked flask, and 750 mL of methanesulfonic acid was added dropwise thereto while cooling in an ice bath such that the internal temperature became 5° C. to 10° C., followed by stirring for 2 hours. Thereafter, 650 g (6.0 mol) of p-cresol was added thereto, followed by stirring at 60° C. for 2 hours. The reaction liquid was cooled to 20° C. in an ice bath, then, 2.5 L of ethanol was added thereto, and the precipitated solid was collected by filtration, whereby 910 g (3.4 mol) of Intermediate 61A was obtained.

$^1$H-NMR (DMSO-d6): 2.25 (s, 3H), 2.30 (s, 3H), 3.55 (s, 3H), 5.19 (s, 1H), 6.8-7.2 (m, 6H)

1.8 L of toluene, 900 g (3.35 mol) of Intermediate 61C, and 540 g (5.0 mol) of m-toluidine were put into a 5 L three-necked flask, followed by stirring at 70° C. for 20 hours. Thereafter, the reaction liquid was cooled to 20° C. in an ice bath, then, 2.0 L of ethanol was added thereto, and the precipitated solid was collected by filtration, whereby 1127 g (3.0 mol) of Intermediate 61B was obtained. $^1$H-NMR (DMSO-d6): 2.18 (s, 3H), 2.21 (s, 3H), 2.28 (s, 3H), 3.74 (s, 3H), 5.58 (s, 1H) 6.6-6.9 (m, 6H), 7.0-7.2 (m, 2H), 7.3-7.6 (m, 2H), 9.24 (s, 1H), 10.09 (s, 1H)

5.0 L of acetone, 1100 g (2.93 mol) of Intermediate 61B, 301 g (1.4 mol) of dibromobutane, and 1200 g (8.8 mol) of potassium carbonate were put into a 10 L three-necked flask, followed by stirring at 60° C. for 24 hours. Thereafter, the reaction liquid was cooled to 20° C. in an ice bath, then, 4.0 L of a 4 N aqueous hydrochloric acid solution was added thereto, and the precipitated solid was collected by filtration. 8.5 L of acetonitrile and the obtained solid were put into a 10 L three-necked flask, followed by stirring at 70° C. for 1 hour. The reaction liquid was cooled to 20° C. in an ice bath, and the solid was collected by filtration, whereby 800 g (1.0 mol) of Intermediate 61C was obtained.

$^1$H-NMR (DMSO-d6): 1.52 (s, 4H), 2.18 (s, 6H), 2.21 (s, 6H), 2.28 (s, 3H), 3.50 (s, 4H), 3.72 (2, 6H), 3.57 (s, 2H), 6.60 (m, 4H), 6.8-7.2 (m, 12H), 7.4-7.6 (m, 4H), 10.08 (s, 2H)

4.0 L of toluene, 800 g (1.0 mol) of Intermediate 61C, and 807 g (8.0 mol) of triethylamine were put into a 10 L three-necked flask, and 460 g (3.0 mol) of phosphorus oxychloride was added dropwise thereto while cooling in an ice bath such that the internal temperature became 15° C. or lower, followed by stirring for 5 hours. Thereafter, after the reaction liquid was cooled to 20° C. in an water bath, a liquid-liquid separation treatment was performed two times with an aqueous 5% NaHCO$_3$ solution, and once with an aqueous 5% NaCl solution, and 100 g of magnesium sulfate was added thereto, followed by stirring for 1 hour. After the magnesium sulfate was removed from the reaction liquid by filtration, the resultant product was concentrated under reduced pressure. Methanol was added to the obtained concentrate, and the precipitated solid was collected by filtration, whereby 615 g (0.8 mol) of Exemplary Compound (61) was obtained.

$^1$H-NMR (DMSO-d6): 1.31 (s, 4H), 2.19 (s, 6H), 2.21 (s, 6H), 2.29 (s, 6H), 3.62 (s, 4H), 3.71 (s, 6H), 6.59 (s, 2H), 6.76 (d, 2H), 6.82 (s, 2H), 6.9-7.3 (m, 14H)

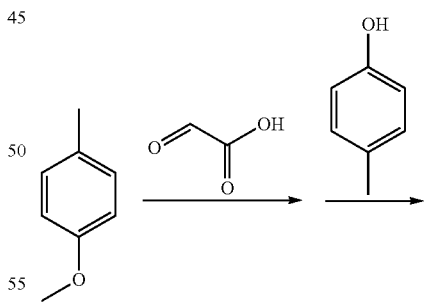

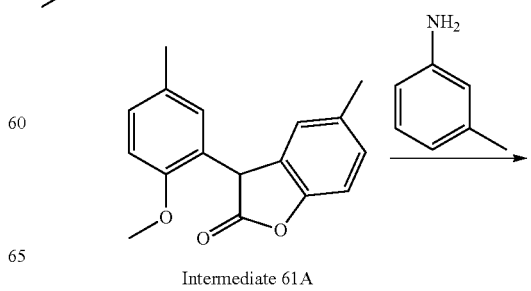

Intermediate 61A

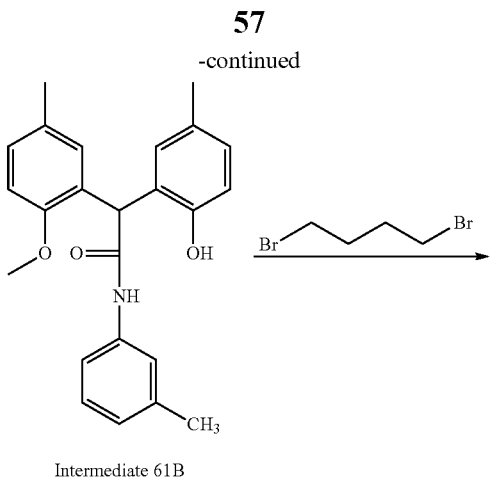

Intermediate 61B

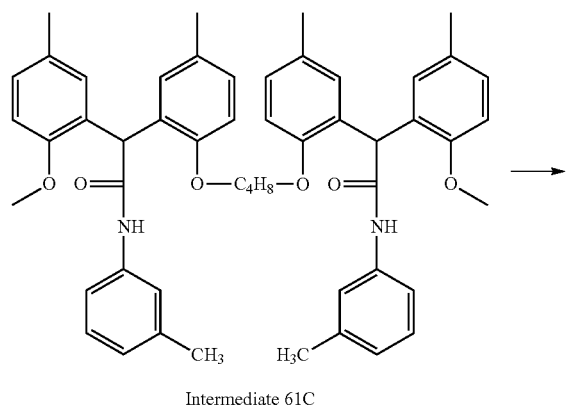

Intermediate 61C

Exemplary Compound (61)

As a ketene imine-based terminal blocking agent, the following compounds were used in each Comparative Example. Moreover, Comparative Example 1 (molecular weight of 269) and Comparative Example 2 (molecular weight of 550) which are ketene inine compounds used in Comparative Example are compounds represented by mono and bis described in Example of Patent Document 1.

Comparative Compound 1

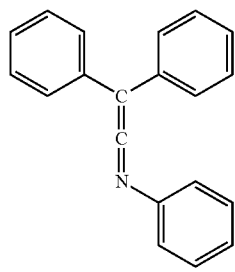

Mw 269

Comparative Compound 2

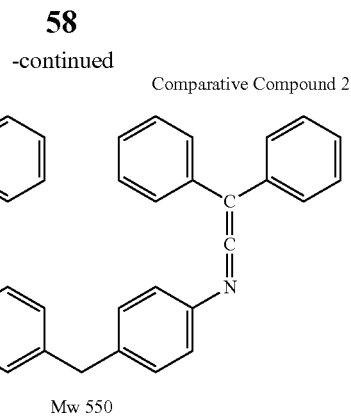

Mw 550

Example 1

1. Preparation of Saturated Polyester Resin

—Step (A)—

4.7 tons of high-purity terephthalic acid and 1.8 tons of ethylene glycol were mixed over 90 minutes to form slurry, and the slurry was continuously supplied to a first esterification reaction tank at a flow rate of 3800 kg/h. Subsequently, an ethylene glycol solution of a citric acid chelated titanium complex (VERTEC AC-420, manufactured by Johnson Matthey Plc.) having Ti metal coordinated with citric acid was continuously supplied to the first esterification reaction tank, and a reaction was performed at a temperature inside the reaction tank of 250° C. and for an average retention time of about 4.4 hours with stirring, thereby obtaining an oligomer. At this time, the citric acid chelated titanium complex was continuously added such that the amount added of Ti was 9 ppm in terms of elements. At this time, the acid value of the oligomer obtained was 500 eq/ton.

The obtained oligomer was transferred to a second esterification reaction tank, and with stirring, the reaction product was allowed to react at a temperature inside the reaction tank of 250° C. for an average retention time of 1.2 hours to obtain an oligomer having an acid value of 180 eq/ton. The inside of the second esterification reaction tank was divided into three zones ranging a first zone to a third zone. At a second zone, an ethylene glycol solution of magnesium acetate was continuously supplied in a manner that the amount added of Mg was 75 ppm in terms of elements. After that, at a third zone, an ethylene glycol solution of trimethyl phosphate was continuously supplied in a manner that the amount added of P was 65 ppm in terms of elements. Moreover, the ethylene glycol solution of trimethyl phosphate was prepared by adding a trimethyl phosphate solution at 25° C. to an ethylene glycol solution at 25° C., followed by stirring at 25° C. for 2 hours (content of phosphorous compounds in the solution: 3.8% by mass).

Thus, an esterification reaction product was obtained.

—Step (B)—

The esterification reaction product obtained in Step (A) was continuously supplied to a first polycondensation reaction tank. Subsequently, polycondensation (transesterification reaction) was performed with stirring the esterification reaction product at a reaction temperature of 270° C. and a pressure inside the reaction tank of 20 torr (2.67×10⁻³ MPa) for an average retention time of about 1.8 hours.

Then, the obtained reaction product was transferred from the first polycondensation reaction tank to a second polycondensation reaction tank. Thereafter, in the second polycondensation reaction tank, the reaction product was subjected to a reaction (transesterification reaction) with stirring under the conditions of a temperature inside the reaction tank of 276° C. and a pressure inside the reaction tank of 5 torr ($6.67 \times 10^{-4}$ MPa) for a retention time of about 1.2 hours.

Subsequently, the reaction product obtained by the transesterification reaction was transferred from the second polycondensation reaction tank to a third polycondensation reaction tank, and in this reaction tank, a reaction (transesterification reaction) was performed with stirring under the conditions of a temperature inside the reaction tank of 276° C. and a pressure inside the reaction tank of 1.5 torr ($2.0 \times 10^{-4}$ MPa) for a retention time of 1.5 hours to obtain a reaction product (polyethylene terephthalate (PET)) having an acid value of 22 eq/ton and an intrinsic viscosity (IV) of 0.65 dl/g.

Furthermore, the obtained PET was subjected to a heat treatment (solid-phase polymerization) at 205° C. for 24 hours under a nitrogen gas flow using a continuous solid-phase polymerizer. Moreover, by increasing the solid-phase polymerization time, IV is easily increased and AV is easily reduced, and by increasing the solid-phase polymerization temperature, the AV is easily increased and the IV is easily reduced.

Thereafter, nitrogen gas of 25° C. is flowed into the vacuum polymerizer, and a pellet was cooled to 25° C., whereby PET having an acid value of 15 eq/ton and an IV of 0.78 dl/g was obtained.

2. Fabrication of Polyester Film and Evaluation

—Extrusion-Molding (Synthesis Step/Film Forming Step)—

The obtained PET was put into a hopper of a twin-screw kneading extruder having a diameter of 50 mm using a main feeder, and Exemplary Compound 1 of the present invention was put into a subfeeder, and melting and extrusion were performed at 280° C. The extruded melt was passed through a gear pump and a filter (pore diameter of 20 μm), and extruded from a die to a cooling roll at 20° C., whereby an amorphous sheet was obtained. Moreover, the extruded melt was adhered to the cooling roll using an electrostatic application method.

—Stretching (Biaxial Stretching Step)—

An unstretched film which was extruded onto the cooling roll and solidified was subjected to sequential biaxial stretching by the following method, whereby a polyester film having a thickness of 175 μm was obtained.

<Stretching Method>

(a) Longitudinal Stretching

The unstretched film is passed through between two pairs of nip rolls having different peripheral speeds, and by this, the unstretched film was stretched in the longitudinal direction (transport direction). Moreover, the stretching was performed at a preheating temperature of 90° C., a stretching temperature of 90° C., a stretching ratio of 3.5 times, and a stretching speed of 3,000%/sec.

(b) Transverse Stretching

The longitudinally stretched film was transversely stretched under the following conditions using a tenter.

<Conditions>

Preheating temperature: 100° C.
Stretching temperature: 110° C.
Stretching ratio: 4.2 times
Stretching speed: 70%/sec —Heat Fixing and Thermal Relaxation—

Subsequently, the stretched film after finishing the longitudinal stretching and transverse stretching was heat-fixed under the following conditions. Furthermore, after heat fixing, the tenter width was shortened and thermal relaxation was performed under the following conditions.

<Heat Fixing Conditions>

Heat fixing temperature: 198° C.
Heat fixing time: 2 seconds

<Thermal Relaxation Conditions>

Thermal relaxation temperature: 195° C.
Thermal relaxation ratio: 5%

—Winding—

After the heat fixing and the thermal relaxation, both ends of the polyester film were trimmed by 10 cm. Thereafter, after knurling 10 mm width of both ends, the polyester film was wound up at a tension of 25 kg/m. Moreover, the width was 1.5 m, and the winding length was 2,000 m.

In the above manner, the polyester film of Example 1 was fabricated. The obtained sample film has a good surface state in which there is no pit or wrinkle.

Examples 2 to 23 and Comparative Examples 1 to 3

A polyester film of each of Examples and Comparative Examples was produced in the same manner as in Example 1 except that the ketene imine compound, the amount added thereof, the addition conditions of the pigment described in the following Table 1 are changed.

—Process Evaluation—

<Volatilization>

A heating treatment was performed on the obtained polyester film at 290° C. for 10 minutes, and the produced gas (ketene imine compound) was detected. The produced gas was evaluated by measuring the amount of the volatile component in the film by gas chromatography (trade name P&T-GC/MS, manufactured by JASCO Corporation). The obtained results are shown in the following Table 1.

A: The amount of gas was 0.1 ppm or less
B: The amount of gas was 0.1 ppm or greater and less than 10 ppm
C: The amount of gas was 10 ppm or greater and less than 1000 ppm
D: The amount of gas was less than 1000 ppm —Performance of Polyester Film—

<Hydrolysis Resistance (PCT Test)>

Hydrolysis resistance (wet heat resistance) was evaluated by a half-life period of a retention rate of tensile elongation at break. The half-life period of a retention rate of tensile elongation at break was evaluated by subjecting the polyester film obtained in Example 1 to a storage treatment (heat treatment) under the conditions of 120° C. and relative humidity of 100% and measuring the storage time when tensile elongation at break (%) shown by the polyester film after storage becomes 50% of tensile elongation at break (%) shown by the polyester film before storage. The obtained results are shown in Table 1 below.

A: The half-life period of tensile elongation at break was 200 hours or greater
B: The half-life period of tensile elongation at break was 170 hours or greater and less than 200 hours
C: The half-life period of tensile elongation at break was 140 hours or greater and less than 170 hours
D: The half-life period of tensile elongation at break was less than 140 hours.

It is shown that as the half-life period of a retention rate of tensile elongation at break is longer, the hydrolysis resistance of the polyester film is excellent. That is, in the polyester film of the present invention, the half-life period of tensile elongation at break before and after the storage treatment under the conditions of 120° C. and relative humidity of 100% is preferably 130 hours or greater, and more preferably 160 hours or greater.

<Color Tone>

Transmittance of the obtained polyester film was measured, and, from this value, the Yellowness Index (YI) value was calculated.

A: YI value was 0 or greater and less than 10
B: YI value was 10 or greater and less than 20
C: YI value was 20 or greater and less than 40
D: YI value was 40 or greater In each of Examples and Comparative Examples, the results obtained from the evaluation described above are shown in the following Table 1. Moreover, in Table 1, the ketene imine value represents the total molecular weight/the number of functional groups of ketene imine.

and when the content ratio of the ketene imine compound is less than 0.1% by mass, sufficient wet heat resistance tends not to be obtained, and when the content of the ketene imine compound is greater than 2.0% by mass, yellowing tends to occur.

Furthermore, it is found that, in a case where the polyester film includes a pigment, in particular, in a case where the polyester film includes titanium oxide, wet heat resistance becomes favorable, and yellowing tends to be suppressed.

On the other hand, it is found that Comparative Examples 1 to 3 include ketene imine compounds which are not represented by Formula (1) described above, and thus, yellowing of the polyester film is significantly occurred. In addition, it is found that, even in a case where the total molecular weight of the ketene imine compound is 500 or greater, volatilization occurs, and the effect of the addition of a pigment is also not obtained.

3. Fabrication of Back Sheet for Solar Cell Module

A back sheet for a solar cell module was fabricated, using the polyester film fabricated in Example 1.

TABLE 1

| | Ketene imine compound | | | | Pigment | | Polyester film performance | | |
|---|---|---|---|---|---|---|---|---|---|
| | Type | Total molecular weight | Ketene imine value | Parts by mass [with respect to polyester] | Type | Parts by mass [with respect to polyester] | Wet heat resistance | Volatility | Color tone |
| Example 1 | Exemplary Compound 1 | 353 | 353 | 1.0 | — | — | A | C | B |
| Example 2 | Exemplary Compound 1 | 353 | 353 | 1.0 | Cacium carbonate | | B | C | B |
| Example 3 | Exemplary Compound 1 | 353 | 353 | 1.0 | Titanium oxide | 5.0 | A | C | A |
| Example 4 | Exemplary Compound 5 | 329 | 329 | 0.1 | — | — | B | B | A |
| Example 5 | Exemplary Compound 5 | 329 | 329 | 0.4 | — | — | A | C | A |
| Example 6 | Exemplary Compound 5 | 329 | 329 | 1.0 | — | — | A | C | A |
| Example 7 | Exemplary Compound 5 | 329 | 329 | 2.0 | — | — | A | C | B |
| Example 8 | Exemplary Compound 5 | 329 | 329 | 1.0 | Titanium oxide | 5.0 | A | C | A |
| Example 9 | Exemplary Compound 18 | 1325 | 331 | 0.1 | — | — | B | A | A |
| Example 10 | Exemplary Compound 18 | 1325 | 331 | 0.4 | — | — | A | A | A |
| Example 11 | Exemplary Compound 18 | 1325 | 331 | 1.0 | — | — | A | A | A |
| Example 12 | Exemplary Compound 18 | 1325 | 331 | 2.0 | — | — | A | A | B |
| Example 13 | Exemplary Compound 18 | 1325 | 331 | 1.0 | Titanium oxide | | A | A | A |
| Example 14 | Exemplary Compound 21 | 639 | 320 | 0.4 | — | — | A | A | A |
| Example 15 | Exemplary Compound 21 | 639 | 320 | 1.0 | — | — | A | A | A |
| Example 16 | Exemplary Compound 21 | 639 | 320 | 1.0 | Titanium oxide | 5.0 | A | A | A |
| Example 17 | Exemplary Compound 22 | 597 | 299 | 1.0 | Titanium oxide | 5.0 | A | A | A |
| Example 18 | Exemplary Compound 41 | 667 | 334 | 0.4 | — | — | A | A | A |
| Example 19 | Exemplary Compound 41 | 667 | 334 | 1.0 | — | — | A | A | A |
| Example 20 | Exemplary Compound 41 | 667 | 334 | 0.4 | Titanium oxide | 5.0 | A | A | A |
| Example 21 | Exemplary Compound 41 | 667 | 334 | 1.0 | Titanium oxide | 5.0 | A | A | A |
| Example 22 | Exemplary Compound 45 | 751 | 376 | 1.0 | Titanium oxide | 5.0 | A | A | A |
| Example 23 | Exemplary Compound 61 | 768 | 384 | 1.0 | Titanium oxide | 5.0 | A | A | A |
| Comparative Example 1 | Comparative Compound 1 | 269 | 269 | 1.0 | — | — | A | D | D |
| Comparative Example 2 | Comparative Compound 2 | 550 | 275 | 1.0 | — | — | A | C | D |
| Comparative Example 3 | Comparative Compound 2 | 550 | 275 | 1.0 | Titanium oxide | 5.0 | C | C | D |

It is found that the polyester films of Examples 1 to 23 include the ketene imine compounds represented by Formula (1) described above, and thus, the polyester films have excellent wet heat resistance (hydrolysis resistance), and yellowing of the polyester films is suppressed. It is found that, among these, the polyester films of Examples 9 to 23 include the ketene imine compounds having the total molecular weight of 500 or greater, and thus, volatilization of the ketene imine compound in the production step is greatly suppressed.

In addition, from the results in Table 1, it is preferable that the content ratio of the ketene imine compound is preferably 0.1% by mass to 2.0% by mass with respect to the polyester, First, a back sheet for a solar cell module of Example 1, which has a reflective layer and a readily adhesive layer on one side of the polyester film fabricated in Example, and has an undercoat layer, a barrier layer, and an antifouling layer on the other side, was fabricated. In a case where the back sheet for a solar cell module obtained in this manner was used in a state of being attached to a solar cell module, the solar cell module exhibited favorable operational performance, and power generation efficiency was not decreased. In addition, in the back sheet for a solar cell module, yellowing did not occur, and favorable design characteristics were maintained.

According to the present invention, by using a ketene imine compound having a specific structure, the hydrolysis resistance of a polyester film is increased, and the polyester film is prevented from being yellowed. Therefore, the polyester resin composition of the present invention can be preferably used as a back sheet for a solar cell module, and has high industrial applicability.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2014/056281, filed on Mar. 11, 2014; Japanese Patent Application No. 2013-049370 filed on Mar. 12, 2013; and Japanese Patent Application No. 2014-008327 filed on Jan. 21, 2014, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

What is claimed is:

1. A polyester resin composition including a ketene imine compound represented by the following Formula (1) and polyester:

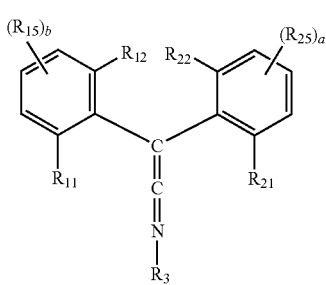

General Formula (1)

wherein, in Formula (1), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent; $R_{15}$ and $R_{25}$ each independently represent an alkyl group which may have a substituent, an aryl group which may have a substituent, an alkoxy group which may have a substituent, or an aryloxy group which may have a substituent; $R_{11}$, $R_{12}$, or $R_{15}$ may form a condensed ring by the substituents adjacent to each other; $R_{21}$, $R_{22}$, or $R_{25}$ may form a condensed ring by the substituents adjacent to each other; $R_3$ represents an alkyl group which may have a substituent or an aryl group which may have a substituent; and a and b each independently represent an integer of 0 to 3.

2. A polyester resin composition including a ketene imine compound represented by the following Formula (2) and polyester:

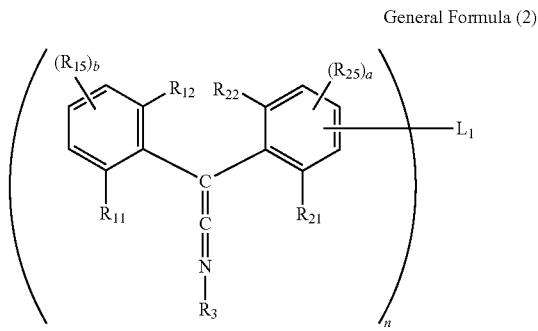

General Formula (2)

wherein, in Formula (2), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent; $R_{15}$ and $R_{25}$ each independently represent an alkyl group which may have a substituent, an aryl group which may have a substituent, an alkoxy group which may have a substituent, or an aryloxy group which may have a substituent; $R_{11}$, $R_{12}$, or $R_{15}$ may form a condensed ring by the substituents adjacent to each other; $R_{21}$, $R_{22}$, or $R_{25}$ may form a condensed ring by the substituents adjacent to each other; $R_3$ represents an alkyl group which may have a substituent or an aryl group which may have a substituent; a represents an integer of 0 to 2; b represents an integer of 0 to 3; n represents an integer of 2 to 4; and $L_1$ represents an n valent linking group.

3. A polyester resin composition including a ketene imine compound represented by the following Formula (3-1) and polyester:

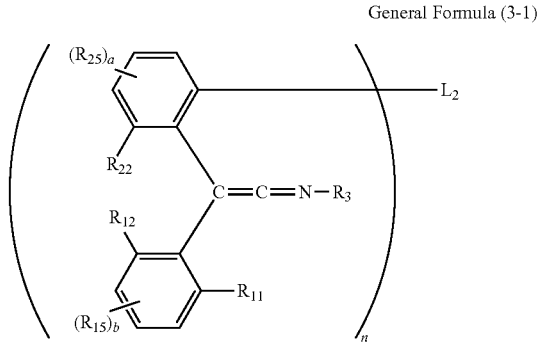

General Formula (3-1)

wherein, in Formula (3-1), at least one of $R_{11}$, $R_{12}$, and $R_{22}$ each independently represents an alkyl group which may have a substituent, an aryl group which may have a substituent, an alkoxy group which may have a substituent, or an aryloxy group which may have a substituent; $R_{15}$ and $R_{25}$ each independently represent an alkyl group which may have a substituent, an aryl group which may have a substituent, an alkoxy group which may have a substituent, or an aryloxy group which may have a substituent; $R_{11}$, $R_{12}$, or $R_{15}$ may form a condensed ring by the substituents adjacent to each other; $R_{22}$ or $R_{25}$ may form a condensed ring by the substituents adjacent to each other; $R_3$ represents an alkyl group which may have a substituent or an aryl group which may have a substituent; a and b each independently represent an integer of 0 to 3; n represents an integer of 2 to 4; and $L_2$ represents an n valent linking group.

4. A polyester resin composition including a ketene imine compound represented by the following Formula (3-2) and polyester:

General Formula (3-2)

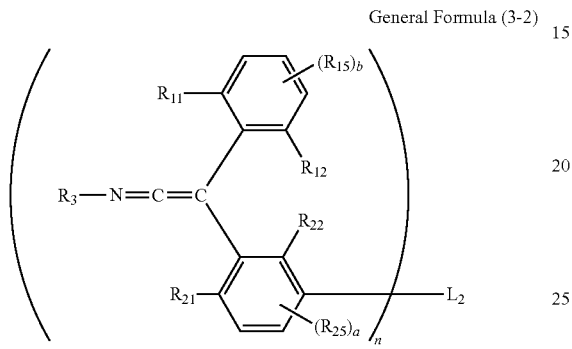

wherein, in Formula (3-2), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent; $R_{15}$ and $R_{25}$ each independently represent an alkyl group which may have a substituent, an aryl group which may have a substituent, an alkoxy group which may have a substituent, or an aryloxy group which may have a substituent; $R_{11}$, $R_{12}$, or $R_{15}$ may form a condensed ring by the substituents adjacent to each other; $R_{21}$ or $R_{25}$ may form a condensed ring by the substituents adjacent to each other; $R_3$ represents an alkyl group which may have a substituent or an aryl group which may have a substituent; a represents an integer of 0 to 2; b represents an integer of 0 to 3; n represents an integer of 2 to 4; and $L_2$ represents an n valent linking group.

5. A polyester resin composition including a ketene imine compound represented by the following Formula (2) and polyester:

General Formula (2)

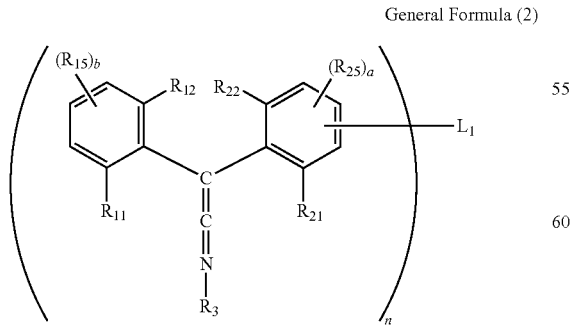

wherein, in Formula (2), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent; $R^{15}$ and $R_{25}$ each independently represent an alkyl group which may have a substituent, an aryl group which may have a substituent, an alkoxy group which may have a substituent, or an aryloxy group which may have a substituent; $R_{11}$, $R_{12}$, or $R_{15}$ may form a condensed ring by the substituents adjacent to each other; $R_{21}$, $R_{22}$, or $R_{25}$ may form a condensed ring by the substituents adjacent to each other; $R_3$ represents an alkyl group which may have a substituent or an aryl group which may have a substituent; a represents an integer of 0 to 2; b represents an integer of 0 to 3; n represents an integer of 2 to 4; and $L_1$ represents an n valent linking group, wherein the ketene imine compound is represented by the following Formula (4):

General Formula (4)

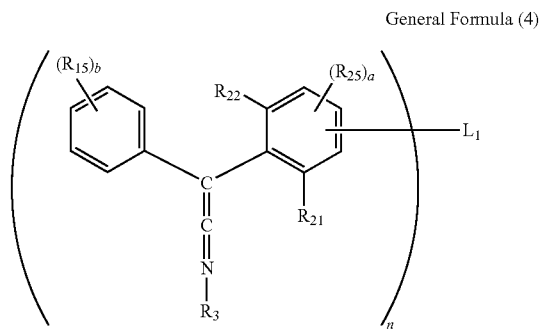

wherein, in Formula (4), at least one of $R_{21}$ and $R_{22}$ each independently represents an alkyl group which may have a substituent, an aryl group which may have a substituent, an alkoxy group which may have a substituent, or an aryloxy group which may have a substituent; $R_{15}$ and $R_{25}$ each independently represent an alkyl group which may have a substituent, an aryl group which may have a substituent, an alkoxy group which may have a substituent, or an aryloxy group which may have a substituent; $R_{15}$ may form a condensed ring by the substituents adjacent to each other; $R_{21}$, $R_{22}$, or $R_{25}$ may form a condensed ring by the substituents adjacent to each other; $R_3$ represents an alkyl group which may have a substituent or an aryl group which may have a substituent; a represents an integer of 0 to 2; b represents an integer of 0 to 5; n represents an integer of 2 to 4; and $L_1$ represents an n valent linking group.

6. The polyester resin composition according to claim 5, wherein at least one of $R_{21}$ and $R_{22}$ in the Formula (4) represents an alkoxy group which may have a substituent or an aryloxy group which may have a substituent.

7. The polyester resin composition according to claim 5, wherein $R_{22}$ in the Formula (4) represents an alkoxy group which may have a substituent or an aryloxy group which may have a substituent.

8. A polyester resin composition including a ketene imine compound represented by the following Formula (2) and polyester:

General Formula (2)

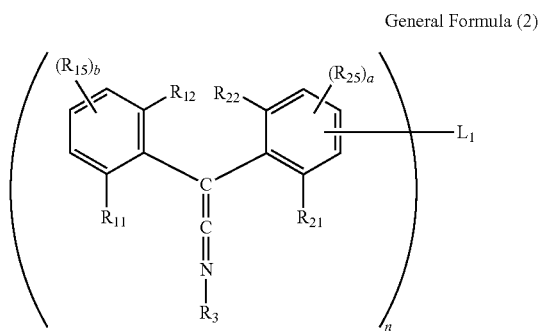

wherein, in Formula (2), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent; $R_{15}$ and $R_{25}$ each independently represent an alkyl group which may have a substituent, an aryl group which may have a substituent, an alkoxy group which may have a substituent, or an aryloxy group which may have a substituent; $R_{11}$, $R_{12}$, or $R_{15}$ may form a condensed ring by the substituents adjacent to each other; $R_{21}$, $R_{22}$, or $R_{25}$ may form a condensed ring by the substituents adjacent to each other; $R_3$ represents an alkyl group which may have a substituent or an aryl group which may have a substituent; a represents an integer of 0 to 2; b represents an integer of 0 to 3; n represents an integer of 2 to 4; and $L_1$ represents an n valent linking group, wherein the ketene imine compound is represented by the following Formula (5):

General Formula (5)

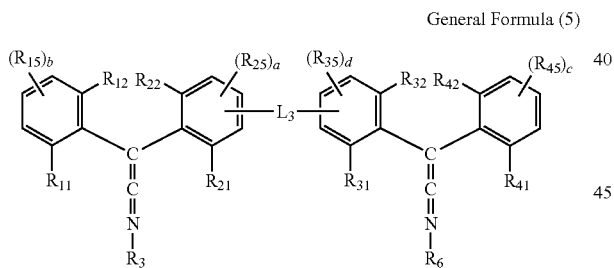

wherein, in Formula (5), at least one of $R_{11}$, $R_{12}$, $R_{21}$, $R_{22}$, $R_{31}$, $R_{32}$, $R_{41}$, and $R_{42}$ each independently represents an alkyl group which may have a substituent, an aryl group which may have a substituent, an alkoxy group which may have a substituent, or an aryloxy group which may have a substituent; $R_{15}$, $R_{25}$, $R_{35}$, and $R_{45}$ each independently represent an alkyl group which may have a substituent, an aryl group which may have a substituent, an alkoxy group which may have a substituent, or an aryloxy group which may have a substituent; $R_{11}$, $R_{12}$, or $R_{15}$ may form a condensed ring by the substituents adjacent to each other; $R_{21}$, $R_{22}$ or $R_{25}$ may form a condensed ring by the substituents adjacent to each other; $R_{31}$, $R_{32}$, or $R_{35}$ may form a condensed ring by the substituents adjacent to each other; $R_{41}$, $R_{42}$, or $R_{45}$ may form a condensed ring by the substituents adjacent to each other; $R_3$ and $R_6$ each represent an alkyl group which may have a substituent or an aryl group which may have a substituent; a and d each independently represent an integer of 0 to 2; b and c each independently represent an integer of 0 to 3; and $L_3$ represents a single bond or a divalent linking group.

9. The polyester resin composition according to claim 8, wherein at least one of $R_{11}$, $R_{12}$, $R_{21}$, $R_{22}$, $R_{31}$, $R_{32}$, $R_{41}$, and $R_{42}$ in the Formula (5) represents an alkoxy group which may have a substituent or an aryloxy group which may have a substituent.

10. The polyester resin composition according to claim 8, wherein at least one of $R_{21}$, $R_{22}$, $R_{31}$, and $R_{32}$ in the Formula (5) represents an alkoxy group which may have a substituent or an aryloxy group which may have a substituent.

11. The polyester resin composition according to claim 1, wherein the ketene imine compound has a molecular weight of 500 or greater.

12. The polyester resin composition according to claim 1, wherein the ketene imine compound has a ketene imine value calculated by the following equation of 420 or less: the total molecular weight/the number of functional groups of ketene imine.

13. The polyester resin composition according to claim 1, wherein the ketene imine compound is contained in 0.1% by mass to 2.0% by mass with respect to the polyester.

14. The polyester resin composition according to claim 1, which further includes a pigment.

15. The polyester resin composition according to claim 14, wherein the pigment is titanium oxide.

16. A polyester film formed of a polyester resin composition including a ketene imine compound represented by the following Formula (1) and polyester:

General Formula (1)

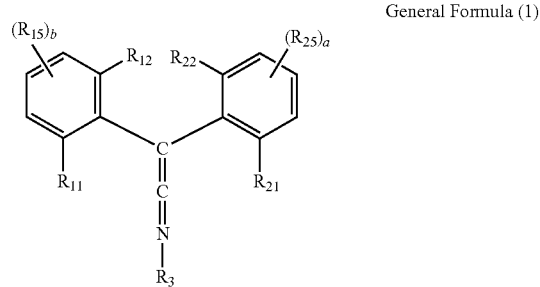

wherein, in Formula (1), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent; $R_{15}$ and $R_{25}$ each independently represent an alkyl group which may have a substituent, an aryl group which may have a substituent, an alkoxy group which may have a substituent, or an aryloxy group which may have a substituent; $R_{11}$, $R_{12}$, or $R_{15}$ may form a condensed ring by the substituents adjacent to each other; $R_{21}$, $R_{22}$, or $R_{25}$ may form a condensed ring by the substituents adjacent to each other; $R_3$ represents an alkyl group which may have a substituent or an aryl group which may have a substituent; and a and b each independently represent an integer of 0 to 3.

17. A back sheet for a solar cell module having a polyester film formed of a polyester resin composition including a ketene imine compound represented by the following Formula (1) and polyester:

General Formula (1)

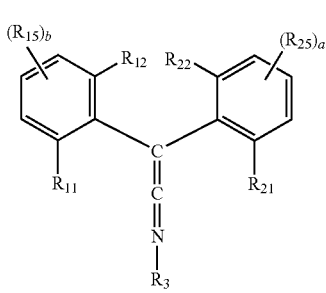

wherein, in Formula (1), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent; $R_{15}$ and $R_{25}$ each independently represent an alkyl group which may have a substituent, an aryl group which may have a substituent, an alkoxy group which may have a substituent, or an aryloxy group which may have a substituent; $R_{11}$, $R_{12}$, or $R_{15}$ may form a condensed ring by the substituents adjacent to each other; $R_{21}$, $R_{22}$, or $R_{25}$ may form a condensed ring by the substituents adjacent to each other; $R_3$ represents an alkyl group which may have a substituent or an aryl group which may have a substituent; and a and b each independently represent an integer of 0 to 3.

18. A solar cell module having a back sheet for a solar cell module having a polyester film formed of a polyester resin composition including a ketene imine compound represented by the following Formula (1) and polyester:

General Formula (1)

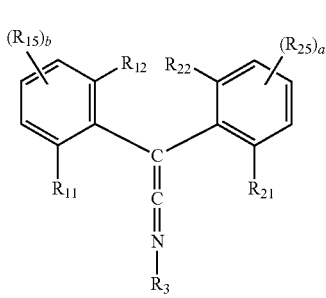

wherein, in Formula (1), at least one of $R_{11}$, $R_{12}$, $R_{21}$, and $R_{22}$ each independently represents an alkyl group which may have a substituent, an aryl group which may have a substituent, an alkoxy group which may have a substituent, or an aryloxy group which may have a substituent; $R_{15}$ and $R_{25}$ each independently represent an alkyl group which may have a substituent, an aryl group which may have a substituent, an alkoxy group which may have a substituent, or an aryloxy group which may have a substituent; $R_{11}$, $R_{12}$, or $R_{15}$ may form a condensed ring by the substituents adjacent to each other; $R_{21}$, $R_{22}$, or $R_{25}$ may form a condensed ring by the substituents adjacent to each other; $R_3$ represents an alkyl group which may have a substituent or an aryl group which may have a substituent; and a and b each independently represent an integer of 0 to 3.

19. A ketene imine compound represented by Formula (6):

General Formula (6)

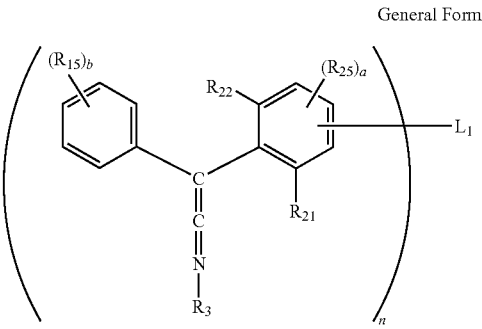

wherein, in Formula (6), at least one of $R_{21}$ and $R_{22}$ represents an alkoxy group which may have a substituent or an aryloxy group which may have a substituent; $R_{15}$ and $R_{25}$ each independently represent an alkyl group which may have a substituent, an aryl group which may have a substituent, an alkoxy group which may have a substituent, or an aryloxy group which may have a substituent; $R_{15}$ may form a condensed ring by the substituents adjacent to each other; $R_{21}$, $R_{22}$, or $R_{25}$ may form a condensed ring by the substituents adjacent to each other; $R_3$ represents an alkyl group which may have a substituent or an aryl group which may have a substituent; a represents an integer of 0 to 2; b represents an integer of 0 to 5; n represents an integer of 2 to 4; and $L_1$ represents an n valent linking group.

20. The ketene imine compound according to claim 19, wherein $R_{22}$ in the Formula (6) represents an alkoxy group which may have a substituent or an aryloxy group which may have a substituent.

21. The ketene imine compound according to claim 19, which is represented by the following Formula (7):

General Formula (7)

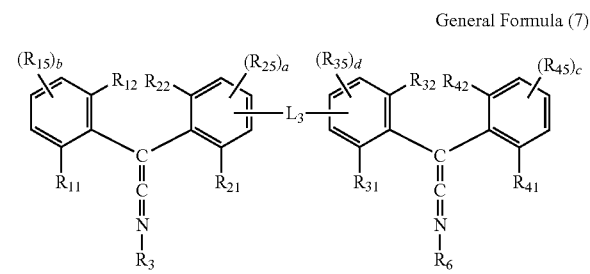

wherein, in Formula (7), at least one of $R_{11}$, $R_{12}$, $R_{21}$, $R_{22}$, $R_{31}$, $R_{32}$, $R_{41}$, and $R_{42}$ represents an alkoxy group which may have a substituent or an aryloxy group which may have a substituent; $R_{15}$, $R_{25}$, $R_{35}$, and $R_{45}$ each independently represent an alkyl group which may have a substituent, an aryl group which may have a substituent, an alkoxy group which may have a substituent, or an aryloxy group which may have a substituent; $R_{11}$, $R_{12}$, or $R_{15}$ may form a condensed ring by the substituents adjacent to each other; $R_{21}$, $R_{22}$ or $R_{25}$ may form a condensed ring by the substituents adjacent to each other; $R_{31}$, $R_{32}$, or $R_{35}$ may form a condensed ring by the substituents adjacent to each other; $R_{41}$, $R_{42}$, or $R_{45}$ may form a condensed ring by the substituents adjacent to each other; $R_3$ and $R_6$ each represent an alkyl group which may have a substituent or an aryl group which may have a substituent; a and d each independently represent an integer of 0 to 2; b and c each independently represent an integer of 0 to 3; and $L_3$ represents a single bond or a divalent linking group.

22. The ketene imine compound according to claim 21, wherein at least one of $R_{21}$, $R_{22}$, $R_{31}$, and $R_{32}$ in the Formula (7) represents an alkoxy group which may have a substituent or an aryloxy group which may have a substituent.

\* \* \* \* \*